(12) United States Patent
Kitada et al.

(10) Patent No.: US 12,064,493 B2
(45) Date of Patent: Aug. 20, 2024

(54) DENTAL PHOTOCURABLE COMPOSITION HAVING EXCELLENT STORAGE STABILITY

(71) Applicant: SHOFU INC., Kyoto (JP)

(72) Inventors: Naoya Kitada, Kyoto (JP); Rei Nishimura, Kyoto (JP); Daisuke Hara, Kyoto (JP); Kenzo Yamamoto, Kyoto (JP)

(73) Assignee: SHOFU INC., Kyoto (JP)

( * ) Notice: Subject to any disclaimer, the term of this patent is extended or adjusted under 35 U.S.C. 154(b) by 121 days.

(21) Appl. No.: 17/692,584

(22) Filed: Mar. 11, 2022

(65) Prior Publication Data

US 2022/0387263 A1 Dec. 8, 2022

(30) Foreign Application Priority Data

| Mar. 12, 2021 | (JP) | 2021-040033 |
| Mar. 12, 2021 | (JP) | 2021-040037 |
| Mar. 12, 2021 | (JP) | 2021-040039 |
| Mar. 12, 2021 | (JP) | 2021-040040 |
| Sep. 14, 2021 | (JP) | 2021-149804 |
| Sep. 14, 2021 | (JP) | 2021-149805 |

(51) Int. Cl.
| *A61K 6/896* | (2020.01) |
| *A61C 5/00* | (2017.01) |
| *A61K 6/17* | (2020.01) |
| *A61K 6/62* | (2020.01) |
| *A61K 6/71* | (2020.01) |
| *A61K 6/76* | (2020.01) |
| *A61K 6/77* | (2020.01) |

(52) U.S. Cl.
CPC ............... *A61K 6/896* (2020.01); *A61C 5/00* (2013.01); *A61K 6/17* (2020.01); *A61K 6/62* (2020.01); *A61K 6/71* (2020.01); *A61K 6/76* (2020.01); *A61K 6/77* (2020.01)

(58) Field of Classification Search
CPC ........................................................ A61K 6/79
See application file for complete search history.

(56) References Cited

U.S. PATENT DOCUMENTS

| 5,846,075 | A | 12/1998 | Suh et al. |
| 7,084,182 | B2 | 8/2006 | Hara et al. |
| 2005/0123762 | A1 | 6/2005 | Ori et al. |
| 2007/0100020 | A1 | 5/2007 | Nakatsuka et al. |
| 2008/0068862 | A1 | 3/2008 | Shimura |
| 2009/0068123 | A1 | 3/2009 | Takei et al. |
| 2010/0267856 | A1 | 10/2010 | Shinoda et al. |
| 2010/0311858 | A1 | 12/2010 | Holmes et al. |
| 2011/0288195 | A1 | 11/2011 | Kajikawa et al. |
| 2017/0355857 | A1 | 12/2017 | Lee et al. |
| 2018/0373145 | A1 | 12/2018 | Shiraishi |
| 2019/0388355 | A1 | 12/2019 | Christensen et al. |
| 2020/0069534 | A1 | 3/2020 | Furuhashi et al. |
| 2021/0283022 | A1 | 9/2021 | Miyata et al. |
| 2022/0002453 | A1 | 1/2022 | Hayakawa et al. |

FOREIGN PATENT DOCUMENTS

| EP | 1 101 484 | 5/2001 |
| EP | 2 163 234 | 3/2010 |
| EP | 2 280 032 | 2/2011 |
| EP | 2 394 628 | 12/2011 |
| EP | 3 398 975 | 11/2018 |
| EP | 3 782 598 | 2/2021 |
| JP | 2001-139843 | 5/2001 |
| JP | 2005-213231 | 8/2005 |
| JP | 2006-76973 | 3/2006 |
| JP | 2006-225350 | 8/2006 |
| JP | 4093974 | 3/2008 |
| JP | 4596786 | 10/2010 |
| JP | 4783151 | 7/2011 |
| JP | 5114498 | 10/2012 |
| JP | 5268478 | 5/2013 |
| JP | 5379563 | 10/2013 |
| JP | 5461415 | 1/2014 |
| JP | 5615720 | 9/2014 |
| JP | 2017-119803 | 7/2017 |
| JP | 2020-500879 | 1/2020 |

(Continued)

OTHER PUBLICATIONS

Extended European Search Report issued Jun. 25, 2021 in corresponding European Patent Application No. 21162475.4.
Extended European Search Report issued Sep. 7, 2021 in corresponding European Patent Application No. 21162481.2.
Extended European Search Report issued Sep. 9, 2021 in corresponding European Patent Application No. 21162479.6.
Extended European Search Report issued Sep. 7, 2021 in corresponding European Patent Application No. 21162490.3.

(Continued)

*Primary Examiner* — Michael F Pepitone
(74) *Attorney, Agent, or Firm* — Wenderoth, Lind & Ponack, L.L.P.

(57) ABSTRACT

To provide a dental photocurable composition having good storage stability of a matrix containing a polymerizable monomer and a polymerization initiator, etc. and excellent mechanical strength of a dental photocurable composition comprising a mixture of the matrix and a filler. The dental photocurable composition of the present disclosure comprises a matrix containing (A) polymerizable monomer, (B) photosensitizer, (C) photoacid generator and (D) photopolymerization accelerator, and (E) filler, wherein, the dental photocurable composition comprises (A1) polymerizable monomer having an acidic group as the (A) polymerizable monomer, and the dental photocurable composition comprises (D1) tertiary aliphatic amine compound having Log P of 2 or more and pKa of 10 or less as the (D) photopolymerization accelerator.

13 Claims, No Drawings

(56) References Cited

FOREIGN PATENT DOCUMENTS

| WO | 99/62460 | 12/1999 |
| WO | 2006/106838 | 10/2006 |
| WO | 2008/068862 | 6/2008 |
| WO | 2018/164074 | 9/2018 |

OTHER PUBLICATIONS

Extended European Search Report issued Sep. 7, 2021 in corresponding European Patent Application No. 21162495.2.
Extended European Search Report issued Aug. 29, 2022 in corresponding European Patent Application No. 22161514.9.
Extended European Search Report issued Aug. 29, 2022 in corresponding European Patent Application No. 22161538.8.
Extended European Search Report issued Aug. 29, 2022 in corresponding European Patent Application No. 22161548.7.
Markus Griesser et al., "Photoinitiators with β-phenylogous Cleavage: an evaluation of reaction mechanisms and performance", Macromolecules, vol. 45, pp. 1737-1745, 2012.

DENTAL PHOTOCURABLE COMPOSITION HAVING EXCELLENT STORAGE STABILITY

CROSS-REFERENCE TO RELATED APPLICATIONS

This application is based on and claims the benefit of priorities from Japanese Patent Application Serial No. 2021-40033 (filed on Mar. 12, 2021), Japanese Patent Application Serial No. 2021-40037 (filed on Mar. 12, 2021), Japanese Patent Application Serial No. 2021-40039 (filed on Mar. 12, 2021), Japanese Patent Application Serial No. 2021-40040 (filed on Mar. 12, 2021), Application Serial No. 2021-149804 (filed on Sep. 14, 2021) and Application Serial No. 2021-149805 (filed on Sep. 14, 2021), the contents of which are hereby incorporated by reference in their entirety.

BACKGROUND OF THE INVENTION

Field of the Invention

The present disclosure relates to a dental photocurable composition.

Description of the Related Art

A dental photocurable composition has been used for treatment of an oral cavity in the dental field, and applied to a dental adhesive material, a dental composite resin, a dental core build-up material, a dental resin cement, a dental coating material, a dental sealant material, a dental manicure material, a dental splinting material, a dental glass ionomer cement, a dental CAD-CAM restoration material, a dental 3D printer material and the like.

In Patent documents 1 and 2, a photopolymerization initiator comprising a photoacid generator (triazine compound or specific aryliodonium salt), a sensitizer, and an electron donor compound is proposed as a photopolymerization initiator.

RELEVANT REFERENCES

Patent Literature

[Patent document 1] Japanese Patent Publication No. 4093974
[Patent document 2] Japanese Patent Publication No. 4596786

SUMMARY OF THE INVENTION

Technical Problem

However, in the dental photocurable compositions using the conventional photopolymerization initiators described in Patent documents 1 and 2, there is a problem in achieving both mechanical strength and storage stability.

An object of the present disclosure is to provide a dental photocurable composition having good storage stability of a matrix containing a polymerizable monomer and a polymerization initiator, etc. and excellent mechanical strength of a dental photocurable composition comprising a mixture of the matrix and a filler.

Solution to Problem

The dental photocurable composition of the present disclosure comprises a matrix containing (A) polymerizable monomer, (B) photosensitizer, (C) photoacid generator and (D) photopolymerization accelerator, and (E) filler, wherein, the dental photocurable composition comprises (A1) polymerizable monomer having an acidic group as the (A) polymerizable monomer, and the dental photocurable composition comprises (D1) tertiary aliphatic amine compound having Log P of 2 or more and pKa of 10 or less as the (D) photopolymerization accelerator.

Advantageous Effects of Invention

The dental photocurable composition of the present disclosure exhibits good storage stability of a matrix and excellent mechanical strength of a dental photocurable composition.

DETAILED DESCRIPTION OF THE PREFERRED EMBODIMENTS

In the present disclosure, the matrix may contain 0.1 to 5 parts by mass of the (A1) polymerizable monomer having an acidic group with respect to 100 parts by mass of the (A) polymerizable monomer contained in the matrix.

In the present disclosure, an electron-withdrawing group may be bonded to one or more of the α-carbon, β-carbon and γ-carbon bonded to N atom derived from amine in the (D1) tertiary aliphatic amine compound having Log P of 2 or more and pKa of 10 or less, and the electron-withdrawing group may be selected from the group consisting of an aryl group, an ester bond and a urethane bond.

In the present disclosure, the dental photocurable composition may comprise an aryl iodonium salt as the (C) photoacid generator.

In the present disclosure, the (B) photosensitizer may contain (B-1) α-diketone compound.

In the present disclosure, the dental photocurable composition may comprise an aryl iodonium salt as the (C) photoacid generator, and the aryl iodonium salt may be a salt of an anion having an organic group in which at least one H is substituted with F and one or more atoms of P, B, Al, S and Ga, and an aryl iodonium cation.

In the present disclosure, the dental photocurable composition may not substantially comprise an aromatic amine compound as the (D) photopolymerization accelerator.

In the present disclosure, the dental photocurable composition may not substantially comprise a tertiary aliphatic amine compound having Log P of less than 2 or pKa of more than 10 as the (D) photopolymerization accelerator.

In the present disclosure, a compounding amount of the (E) filler may be 30 parts by mass or less with respect to 100 parts by mass of the (A) polymerizable monomer contained in the matrix.

In the present disclosure, the dental photocurable composition may comprise, with respect to 100 parts by mass of the (A) polymerizable monomer contained in the matrix, 0.1 to 5 parts by mass of the (A1) polymerizable monomer having an acidic group, 0.02 to 1 parts by mass of the (B) photosensitizer, 0.1 to 5 parts by mass of the (C) photoacid generator, 0.2 to 5 parts by mass of the (D1) tertiary aliphatic amine compound having Log P of 2 or more and pKa of 10 or less, and 1 to 500 parts by mass or more of the (E) filler.

In the present disclosure, the dental photocurable composition may comprise, with respect to 100 parts by mass of the (A) polymerizable monomer contained in the matrix,
0.1 to 5 parts by mass of the (A1) polymerizable monomer having an acidic group,
0.02 to 1 parts by mass of the (B) photosensitizer,
0.1 to 5 parts by mass of the (C) photoacid generator,
0.2 to 5 parts by mass of the (D1) tertiary aliphatic amine compound having Log P of 2 or more and pKa of 10 or less, and
1 to 30 parts by mass or more of the (E) filler.

In the present disclosure, the dental photocurable composition may be used for a dental splinting material.

In the present disclosure, the dental photocurable composition may be prepared by mixing the matrix with the (E) filler after leaving to stand for 2 weeks or more after preparation of the matrix.

In the present disclosure, the dental photocurable composition may comprise a hydrophobized silica fine particle having an average diameter of primary particle of 1 to 40 nm as the (E) filler.

Hereinafter, the dental photocurable composition of the present disclosure is described in detail.

The dental photocurable composition of the present disclosure is applied as a dental adhesive material, a dental composite resin, a dental abutment construction material, a dental resin cement, a dental coating material, a dental pit and fissure plugging material, a dental manicure material, a dental mobile tooth-fixing adhesive material, a dental glass ionomer cement, a dental hard resin, a dental cutting and machining material, a dental 3D printer material and the like.

In a dental practice, in order to restore aesthetically and functionally a lost portion of a tooth by caries, breakages and the like, a direct method which performs restoration with a dental adhesive material and composite resin and an indirect method which restores a prosthetic device consisting of ceramics or dental hard resin with a dental resin cement have been performed as treatment. In addition, a dental adhesive material for mounting a dental composite resin and various dental materials and a natural tooth, a dental splinting material for fixing a mobile tooth, a dental coating material for protecting a vital tooth after forming, against a hyperesthesia, an external stimulation and secondary caries, a dental sealant material for preventing caries by filling deep fissures such as especially a molar tooth, a dental manicure material for temporary recovering aesthetic property by masking discoloration of a tooth, and a dental core build-up material for forming an abutment tooth in the case of collapsing of a dental crown due to caries have been used. In recent years, new composite materials such as a dental restoration material for preparing a prosthetic device by CAD/CAM processing and a dental 3D printer material for preparing a prosthetic device by 3D printer have been developed, and various dental materials have been used for treatment.

The above-described materials are prepared into a uniform paste by mixing a resin matrix consisting of several kinds of polymerizable monomers, a filler such as an inorganic filler and an organic-inorganic composite filler, and a polymerization initiator, according to the application. As one example of some materials, a dental composite resin for filling is used by filling into a tooth in the form of uncured paste, imparting anatomical form of a natural tooth with a dental instrument such as an instrument, and curing by irradiating light with a light irradiator or the like. For the irradiation light from a light irradiator, a light source having an output of about 100 to 2000 mW/cm$^2$ in a wavelength range of about 360 to 500 nm is generally used. On the other hand, a dental resin cement is used for adhering a prosthetic device to a tooth cavity or an abutment tooth, and is cured by light irradiation after attaching the prosthetic device to the tooth cavity or the abutment tooth.

As the photopolymerization initiator used for dental materials, a system in which a photosensitizer and a photosensitizer are combined with an appropriate photopolymerization accelerator has been widely used. As the photosensitizer, acylphosphine oxide compounds and α-diketone compounds are known, and in particular, α-diketone compounds have an ability to initiate polymerization in the wavelength range of visible light which has little effect on the human body. Further, as a compound to be combined with a photosensitizer, a photoacid generator and a tertiary amine compound are well known. A combination of an α-diketone compound, a photoacid generator and a tertiary amine compound has high polymerization activity with respect to irradiation light, and thus has been used in a dental material field. The dental photocurable composition containing this photopolymerization initiator exhibits excellent mechanical properties such as hardness, flexural strength and compressive strength required for various materials.

As typical tertiary amine compounds used as such photoinitiators, aliphatic tertiary amines such as methyl diethanolamine, triethanolamine and dimethylaminoethyl methacrylate, and aromatic tertiary amines such as ethyl dimethylamino benzoate and p-tolylethanolamine are known. Only the combination of a photosensitizer, a photoacid generator and an aromatic tertiary amine compound do not sufficiently satisfy the various properties required for dental materials such as sufficient mechanical strength, sensitivity to light and color tone stability, but photoinitiators consisting of the combination of a photosensitizer, a photoacid generator and an aliphatic tertiary amine compound may satisfy the various properties required for dental materials in a well-balanced manner and therefore are suitable for dental materials.

However, it has been confirmed was that gelation occurs in the matrix containing a photoacid generator, the above-described tertiary aliphatic amine compound and a polymerizable monomer after long-term storage. Usually, a dental photocurable composition is prepared by mixing a matrix and a filler, and there is a case that the matrix is stored for an hour or more in the case of short-term storage and for several years in the long-term storage until the matrix and the filler are mixed. Therefore, there is a case that the mechanical strength immediately after preparation of the dental photocurable composition which is prepared after mixing the matrix with the filler is not sufficient in the case that the degradation rate of matrix is rapid. In addition, the degradation rate differs greatly between the matrix and the paste containing the filler. For example, a matrix may be gelled after one month of standing at 25° C., but there is a case that a paste containing a filler is not gelled at 25° C. for more than three years. This behavior is proportional to the amount of filler, and paste-like compounds with low filler content are prone to gelation as well as matrix.

As a result of studies with using various types of tertiary aliphatic amine compounds to improve the storage stability of a matrix containing a photoacid generator and a tertiary aliphatic amine compound, and it has been found that the Log P and pKa values of a tertiary aliphatic amine compound correlates with the storage stability. The Log P indicates a concentration ratio of molecules in an organic layer and an aqueous layer at equilibrium state, and generally the higher the value, the more hydrophobic the molecule. The pKa is called as the acid deviation constant and is an indicator of the strength of an acid, and the lower the value, the more acidic it is. Furthermore, it has been found that the gelation in the composition is suppressed by containing a polymerizable monomer having an acidic group in the matrix. In other words, it has been found that even if a photoacid generator is contained in a matrix, gelation does not occur during long-term storage by using a tertiary aliphatic amine compound with relatively high hydrophobic having Log P of 2 or more and with an acidity having pKa less than 10 and a polymerizable monomer having an acidic group, and the above problem may be improved, and the present disclosure is completed.

[(A) Polymerizable Monomer]

As the (A) polymerizable monomer contained in the dental photocurable composition of the present disclosure, any polymerizable monomers can be used without limitation as long as it is known. In the polymerizable monomer or the compound having a polymerizable group described in the present disclosure, the polymerizable group preferably exhibits radical polymerizability, and specifically, from the viewpoint of easy radical polymerization, the polymerizable group is preferably (meth) acrylic group and/or (meth) acrylamide group. In the present specification, "(meth) acrylic" means acrylic and/or methacrylic, "(meth) acryloyl" means acryloyl and/or methacryloyl, "(meth) acrylate" means acrylate and/or methacrylate, and, "(meth) acrylamide" means acrylamide and/or methacrylamide. A polymerizable monomer having a substituent at the α-position of an acrylic group and/or an acrylamide group can also be preferably used. Specific examples include one having one radical polymerizable group, one having two radical polymerizable groups, one having three or more radical polymerizable groups, one having an acidic group, one having an alkoxysilyl group, and one having a sulfur atom.

Specific examples of a polymerizable monomer having one radical polymerizable group and not containing acidic group include 2-hydroxyethyl (meth) acrylate, 3-hydroxypropyl (meth) acrylate, 4-hydroxybutyl (meth) acrylate, 2-hydroxypropyl (meth) acrylate, 2-hydroxybutyl (meth) acrylate, 6-hydroxyhexyl (meth) acrylate, 10-hydroxydecyl (meth) acrylate, propylene glycol mono (meth) acrylate, glycerol mono (meth) acrylate, erythritol mono (meth) acrylate, N-methylol (meth) acrylamide, N-hydroxyethyl (meth) acrylamide, N,N-(dihydroxyethyl) (meth) acrylamide, methyl (meth) acrylate, ethyl (meth) acrylate, propyl (meth) acrylate, isopropyl (meth) acrylate, butyl (meth) acrylate, isobutyl (meth) acrylate, benzyl (meth) acrylate, lauryl (meth) acrylate, 2,3-dibromopropyl (meth) acrylate, 3-(meth) acryloyloxypropyl trimethoxysilane, 11-(meth) acryloyloxyundecyl trimethoxysilane, (meth) acrylamide and the like.

Specific Examples of the polymerizable monomer having two radical polymerizable groups and not containing acidic group include 2,2-bis ((meth) acryloyloxy phenyl) propane, 2,2-bis [4-(3-(meth) acryloyloxy)-2-hydroxy propoxyphenyl] propane (generally called "Bis-GMA"), 2,2-bis (4-(meth) acryloyloxy phenyl) propane, 2,2-bis (4-(meth) acryloyloxy polyethoxyphenyl) propane, 2,2-bis (4-(meth) acryloyloxy diethoxyphenyl) propane, 2,2-bis (4-(meth) acryloyloxy tetraethoxyphenyl) propane, 2,2-bis (4-(meth)) acryloyloxy pentaethoxyphenyl) propane, 2,2-bis (4-(meth) acryloyloxy dipropoxyphenyl) propane, 2-(4-(meth) acryloyloxy diethoxyphenyl)-2-(4-(meth) acryloyloxy diethoxyphenyl) propane, 2-(4-(meth) acryloyloxy diethoxyphenyl)-2-(4-(meth) acryloyloxy ditriethoxyphenyl) propane, 2-(4-(meth) acryloyloxy dipropoxyphenyl)-2-(4-(meth) acryloyloxy triethoxyphenyl) propane, 2,2-bis (4-(meth) acryloyloxy propoxyphenyl) propane, 2,2-bis (4-(meth) acryloyloxy isopropoxyphenyl) propane, 1,4-bis (2-(meth) acryloyloxyethyl) pyromellitate, glycerol di (meth) acrylate, 1-(acryloyloxy)-3-(methacryloyloxy)-2-propanol, ethyleneglycol di (meth) acrylate, diethyleneglycol di (meth) acrylate, triethylene glycol di (meth) acrylate, propylene glycol di (meth) acrylate, butylene glycol di (meth) acrylate, neopentyl glycol di (meth) acrylate, polyethylene glycol di (meth) acrylate, 1,3-butanediol di (meth) acrylate, 1,5-pentanediol di (meth) acrylate, 1,6-hexanediol di (meth) acrylate, 1,10-decanediol di (meth) acrylate, 1,2-bis (3-methacryloyloxy-2-hydroxypropoxy) ethane, 2,2,4-trimethyl hexamethylene bis (2-carbamoyloxy ethyl) dimethacrylate (generally called "UDMA"), 1,2-bis (3-methacryloyloxy-2-hydroxy propoxy) ethane and the like.

Specific Examples of the polymerizable monomer having three or more radical polymerizable groups and not containing acidic group include trimethylolpropane tri (meth) acrylate, trimethylolethane tri (meth) acrylate, trimethylolmethane tri (meth) acrylate, pentaerythritol tri (meth) acrylate, pentaerythritol tetra (meth) acrylate, dipentaerythritol penta (meth) acrylate, N,N-(2,2,4-trimethyl hexamethylene) bis [2-(aminocarboxy) propane-1,3-diol] tetra methacrylate, 1,7-diacryloyloxy-2,2,6,6-tetra acryloyloxymethyl-4-oxyheptane and the like.

Specific examples of the polymerizable monomer having an alkoxysilyl group include a (meth) acrylic compound and a (meth) acrylamide compound having one alkoxysilyl group in the molecule and a (meth) acrylic compound and a (meth) acrylamide compound having a plurality of alkoxysilyl groups in the molecule. Specific examples include 2-(meth) acryloxyethyl trimethoxysilane, 3-(meth) acryloxypropyl trimethoxysilane, 3-(meth) acryloxypropyl triethoxysilane, 3-(meth) acryloxypropyl methyldimethoxysilane, 4-(meth) acryloxybutyl trimethoxysilane, 5-(meth) acryloxypentyl trimethoxysilane, 6-(meth) acryloxyhexyl trimethoxysilane, 7-(meth) acryloxyheptyl trimethoxysilane, 8-(meth) acryloxyoctyl trimethoxysilane, 9-(meth) acryloxynonyl trimethoxysilane, 10-(meth) acryloxydecyl trimethoxysilane, 11-(meth) acryloxyundecyl trimethoxysilane. Furthermore, specific examples having an urethane group or an ether group include 3,3-dimethoxy-8,37-dioxo-2,9,36-trioxa-7,38-diaza-3-silatetracontan-40-yl (meth) acrylate, 2-((3,3-dimethoxy-8-oxo-2,9,18-trioxa-7-aza-3-silanonadecane-19-oyl) amino)-2-methylpropane-1,3-diyl di (meth) acrylate, 3,3-dimethoxy-8,19-dioxo-2,9,18-trioxa-7,20-diaza-3-siladocosane-22-yl (meth) acrylate, 3,3-dimethoxy-8,22-dioxo-2,9,12,15,18,21-hexaoxa-7,23-diaza-3-silapentacosane-25-yl (meth) acrylate, 3,3-dimethoxy-8,22-dioxo-2,9,12,15,18,21,26-heptaoxa-7,23-diaza-3-silaoctacosane-28-yl (meth) acrylate, 3,3-dimethoxy-8,19-dioxo-2,9,12,15,18-pentaoxa-7,20-diaza-3-siladocosane-22-yl (meth) acrylate, 3,3-dimethoxy-8,19-dioxo-2,9,12,15,18,23-hexaoxa-7,20-diaza-3-silapentacosane-25-yl (meth) acrylate, 2-((3,3-dimethoxy-8-oxo-2,9,12,15,18-pentaoxa-7-aza-3-silanonadecane-19-oyl) amino)-2-methylpropan-1,3-diyldi (meth) acrylate, 4,4-diethoxy-17-oxo-3,16,21-trioxa-18-aza-4-silatricosane-23-yl (meth) acrylate, 4,4-diethoxy-17-oxo-3,16,21,24-tetraoxa-18-aza-4-silahexacosane-26-yl (meth) acrylate, 4,4-diethoxy-13-oxo-3,12,17-trioxa-14-aza-4-silanonadecane-19-yl (meth) acrylate, 4,4-diethoxy-17-oxo-3,16-dioxa-18-aza-4-silaicosane-20-yl (meth) acrylate and 2-methyl-2-((11-(triethoxysilyl) undecyloxy) carbonylamino) propan-1,3-diyldi (meth) acrylate.

The dental photocurable composition of the present disclosure may contain a polymerizable monomer having a sulfur atom as the (A) polymerizable monomer in order to impart adhesive property with respect to a noble metal. As the polymerizable monomer having a sulfur atom, any known compound can be used without any limitation as long as it is a polymerizable monomer having one or more sulfur atoms and a polymerizable group. Specifically, it refers to a compound having a partial structure such as —SH, —S—S—, >C=S, >C—S—C<, >P=S, or a compound prepared by tautomerism. Specific examples include 10-methacryloxy decyl-6,8-dithiooctanate, 6-methacryloxy hexyl-6,8-dithiooctanate, 6-methacryloxy hexyl-2-thiouracil-5-carboxylate, 2(11-methacryloxy undecylthio)-5-mercapto-1,3,4-thiadiazole, 10-(meth) acryloxy decyl dihydrogenthiophosphate.

An oligomer or a prepolymer having at least one polymerizable group in its molecule may be used other than such a polymerizable monomer, without any limitation. There is no problem even if a substituent such as a fluoro group is contained in the same molecule. The polymerizable monomers described above can be used not only singly but also in combinations of a plurality thereof.

The dental photocurable composition of the present disclosure may contain a silane coupling agent as the (A) polymerizable monomer in order to impart adhesive property with respect to glass ceramics. Any known silane coupling agent can be used without any limitation, but 3-methacryloxypropyl trimethoxysilane, 8-methacryloxyoctyl trimethoxysilane, and 11-methacryloxyundecyl trimethoxysilane and the like are preferable. From the viewpoint of imparting adhesive property, the compounding amount is, with respect to 100 parts by mass of the total amount of the polymerizable monomer contained in the dental photocurable composition, preferably 1 part by mass or more, more preferably 5 parts by mass or more and less than 20 parts by mass. Since the purpose of the silane coupling agent as a polymerizable monomer is to impart adhesive property with respect to glass ceramics or a resin material containing a filler consisting of glass ceramics, the silane coupling agent is compounded separately from the surface treatment agent of the filler.

The dental photocurable composition of the present disclosure may contain a polymerizable monomer having a sulfur atom as the (A) polymerizable monomer in order to impart adhesive property with respect to a noble metal. From the view point of imparting adhesive property, the compounding amount of the polymerizable monomer having a sulfur atom is, with respect to 100 parts by mass of the total amount of the polymerizable monomer contained in the dental photocurable composition, 0.01 part by mass or more, preferably 0.1 parts by mass or more and less than 20 parts by mass.

There is no problem even if a polymerizable monomer having a cationic polymerizable functional group is contained as the polymerizable monomer contained in the dental photocurable composition of the present disclosure, but it is preferable to contain only a polymerizable monomer having a radical polymerizable functional group. When a cationic polymerizable monomer is contained, there is a case that storage stability decrease.

The dental photocurable composition of the present disclosure may contain (A1) polymerizable monomer having an acidic group. For the polymerizable monomer having an acidic group, any polymerizable monomer can be used without any limitation as long as it has one or more polymerizable group and at least one acidic group such as a phosphoric acid group, a pyrophosphoric acid group, a thiophosphoric acid group, a phosphonic acid group, a sulfonic acid group and a carboxylic acid group and the like. It is possible to impart adhesive property with respect to a tooth substance and a prosthetic device by containing a polymerizable monomer having an acidic group. Furthermore, there is a case that storage stability of the matrix is improved when the (A1) polymerizable monomer having an acidic group is contained in the matrix containing the photoacid generator and the tertiary aliphatic amine compound of the present disclosure.

Specific examples of a phosphoric acid group-containing polymerizable monomer include 2-(meth) acryloyloxyethyl dihydrogen phosphate, 3-(meth) acryloyloxypropyl dihydrogen phosphate, 4-(meth) acryloyloxybutyl dihydrogen phosphate, 5-(meth) acryloyloxypentyl dihydrogen phosphate, 6-(meth) acryloyloxyhexyl dihydrogen phosphate, 7-(meth) acryloyloxyheptyl dihydrogen phosphate, 8-(meth) acryloyloxyoctyl dihydrogen phosphate, 9-(meth) acryloyloxynonyl dihydrogen phosphate, 10-(meth) acryloyloxydecyl dihydrogen phosphate, 11-(meth) acryloyloxyundecyl dihydrogen phosphate, 12-(meth) acryloyloxydodecyl dihydrogen phosphate, 16-(meth) acryloyloxyhexadecyl dihydrogen phosphate, 20-(meth) acryloyloxyicosyl dihydrogen phosphate, bis [2-(meth) acryloyl oxyethyl]hydrogensphosphate, bis [4-(meth) acryloyl oxybutyl] hydrogen phosphate, bis [6-(meth) acryloyl oxyhexyl] hydrogen phosphate, bis [8-(meth) acryloyl oxyoctyl] hydrogen phosphate, bis [9-(meth) acryloyl oxynonyl] hydrogen phosphate, bis [10-(meth) acryloyl oxydecyl] hydrogen phosphate, 1,3-di (meth) acryloyl oxypropyl dihydrogenphosphate, 2-(meth) acryloyl oxyethylphenyl hydrogen phosphate, 2-(meth) acryloyloxyethyl-2-bromoethyl hydrogen phosphate and bis [2-(meth) acryloyloxy-(1-hyrdoxymethyl) ethyl]hydrogen phosphate; acyl chloride, alkali metal salt and ammonium salt thereof; and (meth) acrylamide compound in which the ester bond of these compounds is substituted with an amide bond, and the like.

Specific examples of a pyrophosphoric acid group-containing polymerizable monomer include bis [2-(meth) acryloyl oxyethyl] pyrophosphate, bis [4-(meth) acryloyl oxybutyl] pyrophosphate, bis [6-(meth) acryloyl oxyhexyl] pyrophosphate, bis [8-(meth) acryloyl oxyoctyl] pyrophosphate, bis [10-(meth) acryloyl oxydecyl] pyrophosphate; acyl chloride, alkali metal salt and ammonium salt thereof; and (meth) acrylamide compound in which the ester bond of these compounds is substituted with an amide bond, and the like.

Specific examples of a thiophosphate group-containing polymerizable monomer include 2-(meth) acryloyloxyethyl dihydrogen thiophosphate, 3-(meth) acryloyloxypropyl dihydrogen thiophosphate, 4-(meth) acryloyloxybutyl dihydrogen thiophosphate, 5-(meth) acryloyloxypentyl dihydrogen thiophosphate, 6-(meth) acryloyloxyhexyl dihydrogen thiophosphate, 7-(meth) acryloyloxyheptyl dihydrogen thiophosphate, 8-(meth) acryloyloxyoctyl dihydrogen thiophosphate, 9-(meth) acryloyloxynonyl dihydrogen thiophosphate, 10-(meth) acryloyloxydecyl dihydrogen thiophosphate, 11-(meth) acryloyloxyundecyl dihydrogen thiophosphate, 12-(meth) acryloyloxydodecyl dihydrogen thiophosphate, 16-(meth) acryloyloxyhexadecyl dihydrogen thiophosphate, 20-(meth) acryloyloxyicosyl dihydrogen thiophosphate; acyl chloride, alkali metal salt and ammonium salt thereof; and (meth) acrylamide compound in which the ester bond of these compounds is substituted with an amide bond, and the like. The polymerizable monomer having a thiophosphate group is also classified as a polymerizable monomer having a sulfur atom.

Specific examples of a phosphonic acid group-containing polymerizable monomer include 2-(meth) acryloyloxy ethylphenyl phosphonate, 5-(meth) acryloyloxy pentyl-3-phosphonopropionate, 6-(meth) acryloyloxy hexyl-3-phosphonopropionate, 10-(meth) acryloyloxy decyl-3-phosphonopropionate, 6-(meth) acryloyloxy hexyl-3-phosphonoacetate, 10-(meth) acryloyloxy decyl-3-phosphonoacetate; acyl chloride, alkali metal salt and ammonium salt thereof; and (meth)acrylamide compound in which the ester bond of these compounds is substituted with an amide bond, and the like.

Specific examples of a sulfonic acid group-containing polymerizable monomer include 2-(meth) acrylamide-2-methyl propanesulfonic acid and 2-sulfoethyl (meth) acrylate and the like.

The carboxylic acid group-containing polymerizable monomers are classified into a (meth) acrylic-based compound having one carboxyl group in the molecule and a (meth) acrylic-based compound having a plurality of carboxyl groups in the molecule. Examples of the (meth) acrylic-based compound having one carboxyl group in the molecule include (meth) acrylic acid, N-(meth) acryloyl glycine, N-(meth) acryloyl aspartic acid, 0-(meth) acryloyl tyrosine, N-(meth) acryloyl tyrosine, N-(meth) acryloyl phenylalanine, N-(meth) acryloyl-p-aminobenzoic acid, N-(meth) acryloyl-o-aminobenzoic acid, p-vinylbenzoic acid, 2-(meth) acryloyloxybenzoic acid, 3-(meth) acryloyloxybenzoic acid, 4-(meth) acryloyloxybenzoic acid, N-(meth) acryloyl-5-aminosalicylic acid, N-(meth) acryloyl-4-aminosalicylic acid, 2-(meth) acryloyloxyethyl hydrogen succinate, 2-(meth) acryloyloxyethyl hydrogen phthalate, 2-(meth) acryloyloxyethyl hydrogenmalate; acyl chloride thereof; and (meth)acrylamide compound in which the ester bond of these compounds is substituted with an amide bond, and the like. Examples of the (meth) acrylic-based compound having a plurality of carboxyl groups in the molecule include 6-(meth) acryloyl oxyhexane-1,1-dicarboxylic acid, 9-(meth) acryloyl oxynonane-1,1-dicarboxylic acid, 10-(meth) acryloyl oxydecane-1,1-dicarboxylic acid, 11-(meth) acryloyloxy undecane-1,1-dicarboxylic acid, 12-(meth) acryloyl oxydodecane-1,1-dicarboxylic acid, 13-(meth) acryloyloxy tridecane-1,1-dicarboxylic acid, 4-(meth) acryloyloxyethyl trimeritate, 4-(meth) acryloyloxybutyl trimeritate, 4-(meth) acryloyloxyhexyl trimeritate, 4-(meth) acryloyloxydecyl trimeritate, 2-(meth) acryloyl oxyethyl-3'-(meth) acryloyloxy-2'-(3,4-dicarboxy benzoyloxy) propylsuccinate; acid anhydrides and acid halides thereof; and (meth) acrylamide compound in which the ester bond of these compounds is substituted with an amide bond, and the like.

Preferable examples of the (A1) polymerizable monomer having an acidic group include (meth) acrylic acid, 10-methacryloyloxydecyl dihydrogenphosphate, 6-methacryloxyhexyl phosphonoacetate, 4-(meth) acryloyloxyethyl trimeritate and their acid anhydrides. From the view point of imparting adhesive property, the compounding amount of the polymerizable monomer having an acidic group is preferably 0.1 parts by mass or more and 5 parts by mass or less with respect to 100 parts by mass of total amount of the polymerizable monomer contained in the matrix. When the compounding amount is less than 0.1 parts by mass, there is a case that the effect of improving the storage stability of the matrix is not confirmed. When the compounding amount is more than 5 parts by mass, there is a case that a decrease in storage stability or a decrease in photo curability occurs.

In the case of a dental photocurable composition with self-adhesive property that is not used in combination with a primer, a bonding material or an etching material, it is preferable that the compounding amount is 1 part by mass or more with respect to 100 parts by mass of total amount of the polymerizable monomer contained in the matrix. However, in the case of a dental photocurable composition that is used in combination with a primer, a bonding material or an etching material, the material itself is not required to have self-adhesive property, and therefore it is preferable that the compounding amount is 0.1 parts by mass or more and 5 parts by mass or less with respect to 100 parts by mass of total amount of the polymerizable monomer contained in the matrix. Specifically, the matrix may contain 0.1 to 5 parts by mass of the (A1) polymerizable monomer having an acidic group with respect to 100 parts by mass of the (A) polymerizable monomer contained in the matrix. The storage stability of the matrix containing a photoacid generator and an aliphatic amine compound is improved by containing (A1) polymerizable monomer having an acidic group. When the compounding amount is less than 0.1 parts by mass, there is a case that the improving the storage stability is not confirmed. When the compounding amount is more than 5 parts by mass, there is a case that the bendability decreases.

<Photopolymerization Initiator>

The dental photocurable composition of the present disclosure contains a photopolymerization initiator. The photopolymerization initiator is a polymerization initiator that can initiate polymerization by irradiating light. The photopolymerization initiator contained in the dental photocurable composition of the present disclosure contains (B) photosensitizer, (C) photoacid generator, and (D) photopolymerization accelerator. These are not particularly limited, and any known compounds commonly used may be used without any limitation.

[(B) Photosensitizer]

Specific examples of the (B) photosensitizer which can be used in the present disclosure include α-diketones such as benzil, camphorquinone, camphorquinone carboxylic acid, camphorquinone sulfonic acid, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphine oxides such as bis (2,6-dimethoxy benzoyl) phenylphosphine oxide, bis (2,6-dimethoxy benzoyl) (2,4,4-trimethyl pentyl) phosphine oxide, bis (2,6-dimethoxy benzoyl)-n-butylphosphine oxide, bis (2,6-dimethoxy benzoyl)-(2-methylprop-1-yl) phosphine oxide, bis (2,6-dimethoxy benzoyl)-(1-methylprop-1-yl) phosphine oxide, bis (2,6-dimethoxy benzoyl)-t-butyl phosphine oxide, bis (2,6-dimethoxy benzoyl) cyclohexyl phosphine oxide, bis (2,6-dimethoxy benzoyl) octyl phosphine oxide, bis (2-methoxy benzoyl) (2-methylprop-1-yl) phosphine oxide, bis (2-methoxy benzoyl) (1-methylprop-1-yl) phosphine oxide, bis (2,6-diethoxy benzoyl) (2-methylprop-1-yl) phosphine oxide, bis (2,6-diethoxy benzoyl) (1-methylprop-1-yl) phosphine oxide, bis (2,6-dibutoxy benzoyl) (2-methylprop-1-yl) phosphine oxide, bis (2,4-dimethoxy benzoyl) (2-methylprop-1-yl) phosphine oxide, bis (2,4,6-trimethyl benzoyl) phenyl phosphine oxide, 2,4,6-trimethyl benzoyl diphenyl phosphine oxide, bis (2,4,6-trimethyl benzoyl) (2,4-dipentoxy phenyl) phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, 2,6-dimethoxy benzoyl benzyl butyl phosphine oxide, 2,6-dimethoxy benzoyl benzyl octyl phosphine oxide, bis (2,4,6-trimethyl benzoyl) isobutyl phosphine oxide and 2,6-dimethoxy benzoyl-2,4,6-trimethyl benzoyl-n-butyl phosphine oxide; acylgermanium compounds such as bisbenzoyl diethylgermanium, bisbenzoyl dimethylgermanium, bisbenzoyl dibutylgermanium, bis (4-methoxybenzoyl) dimethylgermanium and bis (4-methoxybenzoyl) diethylgermanium; α-aminoacetophenones such as 2-benzyl-dimethylamino-1-(4-morpholinophenyl)-butanone-1, and 2-benzyl-diethylamino-1-(4-morpholinophenyl)-propanone-1; ketals such as benzyl dimethyl ketal, benzyl diethyl ketal and benzyl (2-methoxyethyl ketal); and titanocenes such as bis (cyclopentadienyl)-bis [2,6-difluoro-3-(1-pyrrolyl) phenyl]-titanium, bis (cyclopentadienyl)-bis (pentanefluorophenyl)-titanium and bis (cyclopentadienyl)-bis (2,3,5,6-tetrafluoro-4-disiloxyphenyl)-titanium.

The photosensitizer (B) may be appropriately selected according to the wavelength, the intensity and the irradiation time of light used for polymerization, and the type and the compounding amount of other components to be combined. In addition, the photosensitizer may be used not only singly but also in combinations of two or more. Among them, α-diketone compounds having a maximum absorption wavelength in the visible light region are preferably used, and camphorquinone compounds such as camphorquinone, camphorquinone carboxylic acid and camphorquinone sulfonic acid are more preferable. Camphorquinone is particularly preferred because it is easily available.

Usually, the compounding amount of the (B) photosensitizer with respect to 100 parts by mass of the total amount of the (A) polymerizable monomer contained in the matrix is preferably 0.02 to 1.0 parts by mass, more preferably 0.05 to 0.5 parts by mass. When the compounding amount of the (B) photosensitizer is less than 0.02 parts by mass, there is a case that the polymerization activity with respect to the irradiation light is poor and the curing becomes insufficient. When the compounding amount is more than 1.0 parts by mass, although sufficient curability is exhibited, the sensitivity to light is shortened, and yellowness is increased.

The dental photocurable composition of the present disclosure may contain only the (B-1) α-diketone compounds as the (B) photosensitizer.

[(C) Photoacid Generator]

As the (C) photoacid generator used in the dental photocurable composition of the present disclosure, known compounds can be used without limitation. Specific examples include triazine compounds, iodonium salt compounds, sulfonium salt compounds, and sulfonic acid ester compounds. Among these, triazine compounds and iodonium salt-based compounds are preferable because of having high polymerizability in the case of using in combination with a sensitizer. Iodonium salt-based compounds are more preferable. Iodonium-based salt compounds are susceptible to sensitization by photosensitizers that have absorption in the visible light region.

Specific examples of the triazine compound include 2,4,6-tris (trichloro methyl)-s-triazine, 2,4,6-tris (tribromo methyl)-s-triazine, 2-methyl-4,6-bis (trichloro methyl)-s-triazine, 2-methyl-4,6-bis (tribromo methyl)-s-triazine, 2-phenyl-4,6-bis (trichloro methyl)-s-triazine, 2-(p-methoxy phenyl)-4,6-bis (trichloro methyl)-s-triazine, 2-(p-methyl thiophenyl)-4,6-bis (trichloro methyl)-s-triazine, 2-(p-chloro phenyl)-4,6-bis (trichloro methyl)-s-triazine, 2-(2,4-dichloro phenyl)-4,6-bis (trichloro methyl)-s-triazine, 2-(p-bromo phenyl)-4,6-bis (trichloro methyl)-s-triazine, 2-(p-tolyl)-4,6-bis (trichloro methyl)-s-triazine, 2-n-propyl-4,6-bis (trichloro methyl)-s-triazine, 2-(α,α,ß-trichloro ethyl)-4,6-bis (trichloro methyl)-s-triazine, 2-styryl-4,6-bis (trichloro methyl)-s-triazine, 2-[2-(p-methoxy phenyl) ethenyl]-4,6-bis (trichloro methyl)-s-triazine, 2-[2-(o-methoxy phenyl) ethenyl]-4,6-bis (trichloro methyl)-s-triazine, 2-[2-(p-butoxy phenyl) ethenyl]-4,6-bis (trichloro methyl)-s-triazine, 2-[2-(3,4-dimethoxy phenyl) ethenyl]-4,6-bis (trichloro methyl)-s-triazine, 2-[2-(3,4,5-trimethoxy phenyl) ethenyl]-4,6-bis (trichloro methyl)-s-triazine, 2-(1-naphthyl)-4,6-bis (trichloro methyl)-s-triazine, 2-(4-biphenylyl)-4,6-bis (trichloro methyl)-s-triazine, 2-[2-{N,N-bis(2-hydroxy ethyl) amino} ethoxy]-4,6-bis (trichloro methyl)-s-triazine, 2-[2-{N-hydroxy ethyl-N-ethylamino} ethoxy]-4,6-bis (trichloro methyl)-s-triazine, 2-[2-{N-hydroxy ethyl-N-methylamino} ethoxy]-4,6-bis (trichloro methyl)-s-triazine, 2-[2-{N,N-diallyl amino} ethoxy]-4,6-bis (trichloro methyl)-s-triazine and the like. Among them, 2,4,6-tris (trichloro methyl)-s-triazine is preferable.

Any iodonium salt-based compound can be used as long as it is known. For the specific examples, the structural formula of the iodonium salt-based compound can be represented by the following formula (1).

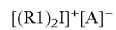

[(R1)₂I]⁺[A]⁻    [Formula (1)]

(In the formula, [(R1)₂I]⁺ is a cation part, [A]⁻ is an anion part, R1 shown in the formula (1) represents an organic group bonded to I, and R1s may be the same or different. R1 represents, for example, an aryl group having 6 to 30 carbon atoms, a heterocyclic group having 4 to 30 carbon atoms, an alkyl group having 1 to 30 carbon atoms, an alkenyl group having 2 to 30 carbon atoms, or an alkynyl group having 2 to 30 carbon atoms, which may have at least one substituted group selected from the group consisting of groups such as alkyl, hydroxy, alkoxy, alkylcarbonyl, arylcarbonyl, alkoxycarbonyl, aryloxycarbonyl, arylthiocarbonyl, acyloxy, arylthio, alkylthio, aryl, heterocycle, aryloxy, alkylsulfinyl, arylsulfinyl, alkylsulfonyl, arylsulfonyl, alkyleneoxy, amino, cyano, nitro groups and halogens.)

In the above, examples of the aryl group having 6 to 30 carbon atoms include a monocyclic aryl group such as a phenyl group and a condensed polycyclic aryl group such as a naphthyl, anthrasenyl, phenanthrenyl, pyrenyl, chrysenyl, naphthacenyl, benzanthrasenyl, anthraquinolyl, fluorenyl, naphthoquinone and anthraquinone.

Examples of the heterocyclic group having 4 to 30 carbon atoms include cyclic groups containing 1 to 3 heteroatoms such as oxygen, nitrogen, and sulfur, which may be the same or different. Specific examples include a monocyclic heterocyclic group such as thienyl, furanyl, pyranyl, pyrrolyl, oxazolyl, thiazolyl, pyridyl, pyrimidyl and pyrazinyl, and a condensed polycyclic heterocyclic group such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl and dibenzofuran.

Specific examples of alkyl groups having 1 to 30 carbon atoms include a linear alkyl group such as methyl, ethyl, propyl, butyl, hexadecyl and octadecyl, a branched alkyl group such as isopropyl, isobutyl, sec-butyl, tert-butyl, isopentyl, neopentyl, tert-pentyl, isohexyl and a cycloalkyl groups such as cyclopropyl, cyclobutyl, cyclopentyl and cyclohexyl.

In addition, specific examples of the alkenyl group having 2 to 30 carbon atoms include a linear chain or branched group such as vinyl, allyl, 1-propenyl, isopropenyl, 1-butenyl, 2-butenyl, 3-butenyl and 1-methyl-1-propenyl.

Further, specific examples of the alkynyl group having 2 to 30 carbon atoms include a linear chain or branched group such as ethynyl, 1-propynyl, 2-propynyl, 1-butynyl, 2-butynyl, 3-butynyl, 1-methyl-1-propynyl and 1-methyl-2-propynyl.

The above-described aryl group having 6 to 30 carbon atoms, heterocyclic group having 4 to 30 carbon atoms, alkyl group having 1 to 30 carbon atoms, alkenyl group having 2 to 30 carbon atoms and alkynyl group having 2 to 30 carbon atoms may have at least one substituted group. Specific examples of the substituted group include a linear alkyl group having 1 to 18 carbon atoms such as methyl, ethyl, propyl, butyl and octadecyl; a branched alkyl group having 1 to 18 carbon atoms such as isopropyl, isobutyl, sec-butyl and tert-butyl; a cycloalkyl group having 3 to 18 carbon atoms such as cyclopropyl, cyclobutyl, cyclopentyl and cyclohexyl; a hydroxy group; a linear chain or branched alkoxy group having 1 to 18 carbon atoms such as methoxy, ethoxy, propoxy, isopropoxy, butoxy, isobutoxy, sec-butoxy, tert-butoxy and dodecyloxy; a linear chain or branched alkylcarbonyl group having 2 to 18 carbon atoms such as acetyl, propionyl, butanoyl, 2-methylpropionyl, heptanoyl, 2-methylbutanoyl, 3-methylbutanoyl and octanoyl; an arylcarbonyl group having 7 to 11 carbon atoms such as benzoyl and naphthoyl; a linear chain or branched alkoxycarbonyl group having 2 to 19 carbon atoms such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl; an aryloxycarbonyl group having 7 to 11 carbon atoms such as phenoxycarbonyl and naphthoxycarbonyl; an arylthiocarbonyl group having 7 to 11 carbon atoms such as phenylthiocarbonyl and naphthoxythiocarbonyl; a linear chain or branched acyloxy group having 2 to 19 carbon atoms such as acetoxy, ethylcarbonyloxy, propylcarbonyloxy, isobutylcarbonyloxy, sec-butylcarbonyloxy, tert-butylcarbonyloxy and octadecylcarbonyloxy; an arylthio group having 6 to 20 carbon atoms such as phenylthio, biphenylthio, methylphenylthio, chlorophenylthio, bromophenylthio, fluorophenylthio, hydroxyphenylthio, methoxyphenylthio, naphthylthio, 4-[4-(phenylthio) benzoyl]phenylthio, 4-[4-(phenylthio) phenoxy] phenylthio, 4-[4-(phenylthio) phenyl] phenylthio, 4-(phenylthio) phenylthio, 4-benzoyl phenylthio, 4-benzoyl-chlorophenylthio, 4-benzoyl-methylthio phenylthio, 4-(methylthiobenzoyl) phenylthio and 4-(p-tert-butylbenzoyl) phenylthio; a linear chain or branched alkylthio group having 1 to 18 carbon atoms such as methylthio, ethylthio, propylthio, tert-butylthio, neopentylthio and dodecylthio; an aryl group having 6 to 10 carbon atoms such as phenyl, tolyl, dimethylphenyl and naphthyl; a heterocycle group having 4 to 20 carbon atoms such as thienyl, furanyl, pyranyl, xanthenyl, chromanyl, isochromanyl, xanthonyl, thioxanthonyl and dibenzofuranyl; an aryloxy group having 6 to 10 carbon atoms such as phenoxy and naphthyloxy; a linear chain or branched alkylsulfinyl group having 1 to 18 carbon atoms such as methylsulfinyl, ethylsulfinyl, propylsulfinyl, tert-pentylsulfinyl and octylsulfinyl; an arylsulfinyl group having 6 to 10 carbon atoms such as phenylsulfinyl, tolylsulfinyl and naphthylsulfinyl; a linear chain or branched alkylsulfonyl group having 1 to 18 carbon atoms such as methylsulfonyl, ethylsulfonyl, propylsulfonyl, isopropylsulfonyl, butylsulfonyl and octylsulfonyl; an arylsulfonyl group having 6 to 10 carbon atoms such as phenylsulfonyl, tolylsulfonyl (tosyl), naphthylsulfonyl; an alkyleneoxy groups; a cyano groups; a nitro groups; and halogens such as fluorine, chlorine, bromine and iodine.

Among the iodonium salt-based compounds, the aryl iodonium salt is preferable because of having high stability. Further, it is preferable that the aryl group has a substituent in order to improve the solubility to the photopolymerization composition. Specifically, a linear alkyl group such as methyl, propyl, octyl, decyl, undecyl, dodecyl and tridecyl, a branched alkyl group such as isopropyl, isobutyl, sec-butyl, tert-butyl, isopentyl, neopentyl, tert-pentyl and isohexyl, a functional group in which one or more of H of these hydrocarbon groups is substituted with F, a perfluoroalkyl group and halogen is suitable as the substituent.

The structure of an anion portion of the iodonium salt-based compound is not particularly limited, and examples include those having atoms such as halogen, P, S, B, Al and Ga. From the viewpoint of safety, anions having As or Sb can be used, but they are not preferable in dental applications. Further, the anion preferably has an organic group such as an alkyl group and/or an alkoxy group and/or an aryl group, and further, most preferably has an organic group such as an alkyl group and/or an alkoxy group and/or an aryl group, in which at least one H is substituted with F. Since the iodonium salt-based compound having such an anion has high solubility in the dental photocurable composition, it is expected to preventing precipitation during low-temperature storage or long-term storage and to shorten the time for preparing due to dissolving in the composition in a short time. Further, an iodonium salt-based compound of an anion having an organic group such as an alkyl group and/or an alkoxy group and/or an aryl group, in which at least one H is substituted with F can be expected to have higher solubility. When the photoacid generator is precipitated, there is a case that it may cause a decrease in color stability after irradiation and a decrease in flexural strength, and therefore it is not preferable. As the anion having an organic group such as an alkyl group and/or an alkoxy group and/or an aryl group, in which at least one H is substituted with F, an anion having any atom can be used. However, from the viewpoint of versatility and safety, those having one or more of P, S, B, Al and Ga are preferable.

Examples of the anion having no alkyl group and/or alkoxy group and/or aryl group include halogens such as chloride and bromide, perhalonic acids such as perchloric acid, aromatic sulfonic acids such as p-toluenesulfonate, camphorsulfonnic acids, nitrates, acetates, chloroacetates, carboxylates, phenolates, tetrafluoroborates, hexafluorophosphates, hexafluoroantimonates, hexafluoroarsenates and the like. Among these, p-toluenesulfonate, camphorsulfonic acid and carboxylate are preferably used.

Since the anionic part of [A]⁻ of the iodonium salt-based compound of the formula (1) improves the solubility to the dental photocurable composition, it is preferable that the anion has an organic group such as alkyl group and/or alkoxy group and/or aryl group, in which at least one His substituted with F. Specifically, the number of carbon atoms of the alkyl group in the anion part of [A]⁻ of the iodonium salt-based compound of the formula (1) is 1 to 8, and preferably 1 to 4. Specific examples include a linear alkyl group such as methyl, ethyl, propyl, butyl, pentyl and octyl, a branched alkyl group such as isopropyl, isobutyl, sec-butyl and tert-butyl, and a cycloalkyl group such as cyclopropyl, cyclobutyl, cyclopentyl and cyclohexyl. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkyl group having a different ratio of a hydrogen atom and a fluorine atom may be compounded in the dental photocurable composition.

Further, specific examples of the alkyl group include a linear chain or branched perfluoroalkyl group such as $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $(CF_3)_3C$.

The number of carbon atoms of the alkyl group in the anion part of $[A]^-$ of the iodonium salt-based compound of the formula (1) is 1 to 8, and preferably 1 to 4. Specific examples include a linear alkoxy group such as methoxy, ethoxy, propoxy, butoxy, pentoxy and octoxy, and a branched alkoxy group such as isopropoxy, isobutoxy, sec-butoxy and tert-butoxy. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkoxy group having a different ratio of a hydrogen atom and a fluorine atom may be compounded in the dental photocurable composition.

Further, specific examples of the alkoxy group include a linear or branched perfluoroalkoxy group such as $CF_3O$, $CF_3CF_2O$, $CF_3CF_2CF_2O$, $(CF_3)_2CFO$, $CF_3CF_2CF_2CF_2$), $(CF_3)_2CFCF_2O$, $CF_3CF_2(CF_3)CFO$, $CF_3CF_2CF_2CF_2CF_2O$ and $CF_3CF_2CF_2CF_2CF_2CF_2CF_2CF_2O$.

The phenyl group in the anion part of $[A]^-$ of the iodonium salt compound of the formula (1) may be a phenyl group, in which at least one H is substituted with fluorine atom, an alkyl group and/or an alkoxy group substituted with fluorine atom. The alkyl group and/or alkoxy group substituted with fluorine atom are preferably those described above. Specific examples of particularly preferable phenyl group include perfluorophenyl group such as pentafluorophenyl group $(C_6F_5)$, trifluorophenyl group $(C_6H_2F_3)$, tetrafluorophenyl group $(C_6HF_4)$, trifluoromethylphenyl group $(CF_3C_6H_4)$, bis (trifluoromethyl) phenyl group $((CF_3)_2C_6H_3)$, pentafluoroethyl phenyl group $(CF_3CF_2C_6H_4)$, bis (pentafluoroethyl) phenyl group $((CF_3)_2C_6H_3)$, trifluoromethyl fluorophenyl group $(CF_3C_6H_3F)$, bistrifluoromethyl fluorophenyl group $((CF_3)_2C_6H_2F)$, pentafluoroethyl fluorophenyl group $(CF_3CF_2C_6H_3F)$, bispentafluoroethyl fluorophenyl group $(CF_3CF_2)_2C_6H_2F$ and the like. An iodonium salt consisting of an anion having a phenyl group having a different ratio of a hydrogen atom and a fluorine atom may be compounded in the dental photocurable composition.

As specific examples of the anion portion of $[A]^-$ of the iodonium salt compound of the formula (1), examples of the anion having P include $[(CF_3CF_2)_3PF_3]^-$, $[(CF_3CF_2CF_2)_3PF_3]^-$, $[((CF_3)_2CF)_2PF_4]^-$, $[((CF_3)_2CF)_3PF_3]^-$, $[((CF_3)_2CF)_4PF_2]^-$, $[((CF_3)_2CFCF_2)_2PF_4]^-$, $[((CF_3)_2CFCF_2)_3PF_3]^-$ and the like. Examples of the anion having S include $[(CF_3SO_2)_3C]^-$, $[(CF_3CF_2SO_2)_3C]^-$, $[(CF_3CF_2CF_2SO_2)_3C]^-$, $[(CF_3CF_2CF_2CF_2SO_2)_3C]^-$, $[CF_3CF_2CF_2CF_2SO_3]^-$, $[CF_3CF_2CF_2SO_3]^-$, $[(CF_3CF_2SO_2)_3C]^-$, $[(SO_2CF_3)_3N]^-$, $[(SO_2CF_2CF_3)_2N]^-$, $[((CF_3)C_6H_4)SO_3]^-$, $[SO_3(CF_2CF_2CF_2CF_2)SO_3]^{2-}$ and the like. Examples of the anion having B include $[B(C_6F_5)_4]^-$, $[(C_6H_5)B((CF_3)_2C_6H_3)_3]^-$, $[(C_6H_5)B(C_6F_5)_3]^-$ and the like. Examples of an anion having Ga include $[((CF_3)_4Ga)]^-$, $[Ga(C_6F_5)_4]^-$ and the like. Examples of anions having Al include $[((CF_3)_3CO)_4Al]^-$, $[((CF_3CF_2)_3CO)_4Al]^-$.

The compounding amount of the (C) photoacid generator in the dental photocurable composition of the present disclosure is preferably 0.1 to 5 parts by mass or more, more preferably 0.2 to 5 parts by mass or more, with respect to 100 parts by mass of the total amount of the (A) polymerizable monomer. When the compounding amount of the photoacid generator is less than 0.1 parts by mass, there is a case that the polymerization promoting ability is poor and the curing becomes insufficient. When the compounding amount is more than 5 parts by mass, although sufficient curability is exhibited, there is a case that the sensitivity to light is lowered to shorten operation time, and discoloration such as browning of the cured body increases.

The photoacid generator that can be used in the dental photocurable composition of the present disclosure is not limited to the photoacid generator described in the specific example, and two or more types can be used in combination.

The dental photocurable composition of the present disclosure may comprise only an aryl iodonium salt which is a salt of an anion having an organic group and one or more atoms of P, B, Al, S, and Ga, and an aryl iodonium cation as the (C) photoacid generator. The dental photocurable composition of the present disclosure may comprise only an aryl iodonium salt which is a salt of an anion having an organic group in which at least one H may be substituted with F and one or more atoms of P, B, Al, S, and Ga, and an aryl iodonium cation as the (C) photoacid generator.

[(D) Photopolymerization Accelerator]

The (D) photopolymerization accelerator which is used for the dental photocurable composition of the present disclosure is not particularly limited as long as it has polymerization promoting ability, and any known photopolymerization accelerator commonly used in the dental field may be used without any limitation. As the photopolymerization accelerator, a primary to tertiary amine compound such as an aromatic amine compound and an aliphatic amine compound, a phosphine compound, an organic metal compound, a transition metal compound of the group 4 in the periodic table, a thiourea derivative, a sulfinic acid and a salt thereof, a borate compound, a sulfur-containing reductive inorganic compound, a nitrogen-containing reductive inorganic compound, a barbituric acid derivative, a triazine compound, a halogen compound and the like can be used.

Aromatic amine compound refers to a compound in which one or more H of ammonia ($NH_3$) is replaced with an aromatic ring. Aromatic amine compound in which one H of $NH_3$ is substituted with an aromatic ring is classified into an aromatic primary amine compound, aromatic amine compound in which one H of $NH_3$ is substituted with an aromatic ring and one H of remaining two H is substituted with an aromatic ring or an alkyl group is classified into an aromatic secondary amine compound, and aromatic amine compound in which one H of $NH_3$ is substituted with an aromatic ring and remaining two H are substituted with an aromatic ring or an alkyl group is classified into an aromatic tertiary amine compound.

Specific examples of the aromatic primary amine compound include aniline. Specific examples of the aromatic secondary amine compound include N-protected amino acid (ester) such as N-phenyl benzylamine, N-benzyl-p-anisidine, N-benzyl-o-phenetidine, N-phenylglycine ethyl and N-phenylglycine. Specific examples of the aromatic tertiary amine compound include N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylamino benzaldehyde, p-dimethylamino acetophenone, p-dimethylamino benzoic acid, p-dimethylamino benzoic acid ethyl ester, p-dimethylamino benzoic acid isoamyl estel, p-dimethylamino benzoic acid 2-butoxyethyl, p-dimethylamino benzoic acid 2-ethylhexyl, p-dimethylamino benzoic acid amino ester, N,N-dimethyl anthranic acid methyl ester, N,N-dihydroxyethyl aniline, N,N-diisopropanol aniline, p-N,N-dihydroxyethyl-toluidine, p-N,N-dihydroxypropyl-toluidine, p-dimethylamino phenyl alcohol, p-dimethylamino styrene, N,N-dimethyl-3,5-xylidine, 4-dimethylamino pyridine, N,N-dimethyl-α-naphthylamine, N,N-dimethyl-ß-naphthylamine and the like. Among them, p-dimethylamino benzoic acid ethyl ester is preferable.

The phosphine compound refers to a compound which is trisubstituted on P atom with organic groups, and the aromatic phosphine compound refers to a compound which is substituted on P atom with a phenyl group which may have one or more substituents. Specific examples of the phosphine compound include trimethylphosphine, tributylphosphine, trihexylphosphine, tri-n-octylphosphine, tricyclohexylphosphine, tri (2-thienyl) phosphine, diphenylpropyl phosphine, di-tert-butyl (3-methyl-2-butenyl) phosphine, methyldiphenyl phosphine, triphenyl phosphine, 2-(diphenylphosphino) styrene, 3-(diphenylphosphino) styrene, 4-(diphenylphosphino) styrene, allyldiphenyl phosphine, 2-(diphenylphosphino) benzaldehyde, 3-(diphenylphosphino) benzaldehyde, 4-(diphenylphosphino) benzaldehyde, 2-(phenylphosphine) benzoic acid, 3-(phenylphosphino) benzoic acid, 4-(phenylphosphino) benzoic acid, tris (2-methoxyphenyl) phosphine, tris (3-methoxyphenyl) phosphine, tris (4-methoxyphenyl) phosphine, 2-(diphenylphosphino) biphenyl, tris (4-fluorophenyl) phosphine, tri (o-trill) phosphine, tri (m-trill) phosphine, tri (p-trill) phosphine, 2-(dimethylamino) phenyldiphenyl phosphine, 3-(dimethylamino) phenyldiphenyl phosphine, 4-(dimethylamino) phenyldiphenyl phosphine, 2,2'-bis (diphenylphosphino) biphenyl, bis [2-(diphenylphosphino) phenyl] ether and the like. Among them, triphenylphosphine, 4-(phenylphosphino) benzoic acid, tri (o-tolyl) phosphine, tri (m-tolyl) phosphine and tri (p-tolyl) phosphine are preferable.

Aliphatic amine compounds refer to compounds in which one or more H of ammonia ($NH_3$) are substituted with alkyl group. As for the alkyl group, $CH_3$— and —$CH_2$— are classified as a primary alkyl group, the one in which one H of —$CH_2$— is substituted with a substituent is classified as a secondary alkyl group, and the one in which two H of —$CH_2$— are substituted with substituents is classified as a tertiary alkyl group. Aliphatic amine in which one H of $NH_3$ is substituted with an alkyl group is classified into an aliphatic primary amine compound, aliphatic amine compound in which two H of $NH_3$ are substituted with an alkyl group is classified into an aliphatic secondary amine compound, and aliphatic amine compound in which three H of $NH_3$ are substituted with an alkyl group is classified into an aliphatic tertiary amine compound.

Specific examples of the aliphatic primary amine compound include amino acid or amino acid ester such as benzhydrylamine, triphenylmethylamine and glycine. Specific examples of the aliphatic secondary amine compound include dibenzylamine, N-benzyl-1-phenylethylamine, bis (1-phenylethyl) amine, bis (4-cyanobenzyl) amine, N-benzyl protected amino acid and N-benzyl protected amino acid ester. Specific examples of the aliphatic tertiary amine compound include tributylamine, tripropylamine, triethylamine, N,N-dimethyl hexylamine, N,N-dimethyl dodecylamine, N,N-dimethyl stearylamine, N-[3-(dimethylamino) propyl] acrylamide, N,N-dimethyl formamide dimethylacetal, N,N-dimethylacetamide dimethylacetal, N,N-dimethylformamide diethylacetal, N,N-dimethylformamide dipropylacetal, N,N-dimethylformamide di-tert-butylacetal, 1-(2-hydroxyethyl) ethyleneimine, N,N-dimethyl ethanolamine, N,N-dimethyl isopropanolamine, N,N-diisopropyl ethanolamine, N-methyl diethanolamine, N-ethyl diethanolamine, N-ethyl diethanolamine, N-butyl diethanolamine, N-lauryl diethanolamine, N-stearyl diethanolamine, triethanolamine, triisopropanolamine, tribenzylamine, dibenzylglycine ethylester, N'-(2-hydroxyethyl)-N,N,N'-trimethylethylene diamine, 2-(dimethylamino)-2-methyl-1-propanol, N,N-dimethyl-2,3-dihydroxypropylamine, N,N-diethylethanolamine, 1-methyl-3-pyrrolidinol, 1-(2-hydroxyethyl) pyrrolidine, 1-isopropyl-3-pyrrolidinol, 1-piperidin ethanol, 2-[2-(dimethylamino) ethoxy] ethanol, N,N-dimethylglycine, N,N-dimethylglycine methyl, N,N-diethylglycine methyl, N,N-dimethylglycine ethyl, N,N-diethylglycine sodium, 2-(dimethylamino) ethylacetate, N-methylimimino diacetic acid, N,N-dimethylamino ethylacrylate, N,N-diethylamino ethylmethacrylate, N,N-diisopropylamino ethylmethacrylate, N,N-dibutylamino ethylmethacrylate, N,N-dibenzylamino ethylmethacrylate, 3-dimethylamino propionitrile, tris (2-cyanoethyl) amine, N,N-dimethyl allylamine, N,N-diethyl allylamine and triallylamine.

Specific examples of the above organic metal compound include an organic metal compound containing scandium (Sc), titanium (Ti), vanadium (V), manganese (Mn), iron (Fe), cobalt (Co), nickel (Ni), copper (Cu), tin (Sn), zinc (Zn) an/or zirconia (Zr), and an organic metal compound containing tin (Sn), vanadium (V) and/or copper (Cu) is preferable. Specific examples of the organic metal compound containing tin (Sn) include dibutyl-tin-diacetate, dibutyl-tin-dimaleate, dioctyl-tin-dimaleate, dioctyl-tin-dilaurate, dibutyl-tin-dilaurate, dioctyl-tin-diversate, dioctyl-tin-S,S'-bis-isooctyl mercapto acetate, tetramethyl-1,3-diacetoxy distanoxane and the like. Specific examples of the organic metal compound containing vanadyl (V) include acetylacetone vanadium, divanadium tetraoxide, vanadyl acetylacetonate, vanadyl stearate oxide, vanadyl oxalate, vanadyl sulphate, oxobis (1-phenyl-1,3-butandionate) vanadium, bis (maltlate) oxovanadium, vanadium pentoxide and sodium metavanadate. Specific examples of the organic metal compound containing copper (Cu) include copper acetylacetone, copper naphthenate, copper octylate, copper stearate and copper acetate.

Among these, a trivalent or tetravalent vanadium compound and a divalent copper compound are preferable. Among them, because of having higher polymerization accelerating ability, a trivalent or tetravalent vanadium compound is more preferable, and a tetravalent vanadium compound is most preferable. A plurality of kinds of these transition metal compounds in the period 4 in the periodic table may be used in combination, if necessary. The compounding amount of transition metal compound is preferably 0.0001 to 1 parts by mass with respect to 100 parts by mass of the total amount of the (A) polymerizable monomer. When the compounding amount is less than 0.0001 parts by mass, there is a case where the polymerization accelerating effect is insufficient, and when the compounding amount exceeds 1 part by mass, there is a case where it causes discoloration or gelation of the dental photocurable composition and the storage stability is lowered.

Any known thiourea derivatives can be used as the thiourea derivative without any limitation. Specific examples of the thiourea derivatives include dimethylthiourea, diethylthiourea, tetramethylthiourea, (2-pyridyl) thiourea, N-methylthiourea, ethylenethiourea, N-allylthiourea, N-allyl-N'-(2-hydroxyethyl) thiourea, N-benzylthiourea, 1,3-dicyclohexyl thiourea, N,N'-diphenylthiourea, 1,3-di (p-tolyl) thiourea, 1-methyl-3-phenylthiourea, N-acetylthiourea, N-benzoylthiourea, diphenylthiourea, dicyclohexylthiourea and the like. Among these, (2-pyridyl) thiourea, N-acetylthiourea and N-benzoylthiourea are preferable. A plurality of kinds of these thiourea derivatives can be used in combination, if necessary. The compounding amount of the thiourea derivative is preferably 0.1 to 5 parts by mass with respect to 100 parts by mass of the total amount of the (A) polymerizable monomers. When the compounding amount is less than 0.1 parts by mass, there is a case where the ability as a polymerization accelerator is insufficient, and when the compounding amount exceeds 5 parts by mass, the storage stability may be lowered.

Examples of sulfinic acid and its salt include p-toluene sulfinic acid, sodium p-toluene sulfinate, potassium p-toluene sulfinate, lithium p-toluene sulfinate, calcium p-toluene sulfinate, benzenesulfinic acid, sodium benzene sulfinate, potassium benzene sulfinate, lithium benzenesulfinate, calcium benzenesulfinate, 2,4,6-trimethyl benzenesulfinic acid, sodium 2,4,6-trimethyl benzenesulfinate, potassium 2,4,6-trimethyl benzenesulfinate, lithium 2,4,6-trimethyl benzenesulfinate, calcium 2,4,6-trimethyl benzenesulfinate, 2,4,6-triethyl benzenesulfinic acid, sodium 2,4,6-triethyl benzenesulfinate, potassium 2,4,6-triethyl benzenesulfinate, lithium 2,4,6-triethyl benzenesulfinate, calcium 2,4,6-triethyl benzenesulfinate, 2,4,6-triisopropyl benzenesulfinic acid, sodium 2,4,6-triisopropyl benzenesulfinate, potassium 2,4,6-triisopropylbenzenesulfinate, lithium 2,4,6-triisopropylbenzenesulfinate, calcium 2,4,6-triisopropyl benzenesulfinate and the like. Among them, sodium benzenesulfinate, sodium p-toluenesulfinate, and sodium 2,4,6-triisopropyl benzenesulfinate are particularly preferable.

As the borate compound, specific examples of the borate compound having one aryl group in one molecule include trialkylphenylboron, trialkyl (p-chlorophenyl) boron, trialkyl (p-fluorophenyl) boron, trialkyl (3,5-bistrifluoro methyl) phenyl boron, trialkyl [3,5-bis (1,1,1,3,3,3-hexafluoro-2-methoxy-2-propyl) phenyl] boron, trialkyl (p-nitrophenyl) boron, trialkyl (m-nitrophenyl) boron, trialkyl (p-butylphenyl) boron, trialkyl (m-butylphenyl) boron, trialkyl (p-butyloxyphenyl) boron, trialkyl (m-butyloxyphenyl) boron, trialkyl (p-octyloxyphenyl) boron and trialkyl (m-octyloxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having two aryl groups in one molecule include dialkyl diphenylboron, dialkyl di (p-chlorophenyl) boron, dialkyl di (p-fluorophenyl) boron, dialkyl di (3,5-bistrifluoro methyl) phenyl boron, dialkyl di [3,5-bis (1,1,1,3,3,3-hexafluoro-2-methoxy-2-propyl) phenyl] boron, dialkyl di (p-nitrophenyl) boron, dialkyl di (m-nitrophenyl) boron, dialkyl di (p-butylphenyl) boron, dialkyl di (m-butylphenyl) boron, dialkyl di (p-butyl oxyphenyl) boron, dialkyl di (m-butyl oxyphenyl) boron, dialkyl di (p-octyl oxyphenyl) boron and dialkyl di (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having three aryl groups in one molecule include monoalkyl triphenylboron, monoalkyl tri (p-chlorophenyl) boron, monoalkyl tri (p-fluorophenyl) boron, monoalkyl tri (3,5-bistrifluoro methyl) phenyl boron, monoalkyl tri [3,5-bis (1,1,1,3,3,3-hexafluoro-2-methoxy-2-propyl) phenyl] boron, monoalkyl tri (p-nitrophenyl) boron, monoalkyl tri (m-nitrophenyl) boron, monoalkyl tri (p-butylphenyl) boron, monoalkyl tri (m-butylphenyl) boron, monoalkyl tri (p-butyl oxyphenyl) boron, monoalkyl tri (m-butyl oxyphenyl) boron, monoalkyl tri (p-octyl oxyphenyl) boron and monoalkyl tri (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having four aryl groups in one molecule include tetraphenylboron, tetra kis (p-chlorophenyl) boron, tetra kis (p-fluorophenyl) boron, tetra kis (3,5-bistrifluoro methyl) phenyl boron, tetra kis [3,5-bis (1,1,1,3,3,3-hexafluoro-2-methoxy-2-propyl) phenyl] boron, tetra kis (p-nitrophenyl) boron, tetra kis (m-nitrophenyl) boron, tetra kis (p-butylphenyl) boron, tetra kis (m-butylphenyl) boron, tetra kis (p-butyl oxyphenyl) boron, tetra kis (m-butyl oxyphenyl) boron, tetra kis (p-octyl oxyphenyl) boron, tetra kis (m-octyl oxyphenyl) boron, (p-fluorophenyl) triphenylboron, (3,5-bis trifluoromethyl) phenyl triphenylboron, (p-nitrophenyl) triphenylboron, (m-butyl oxyphenyl) triphenylboron, (p-butyl oxyphenyl) triphenylboron, (m-octyl oxyphenyl) triphenylboron and (p-octyl oxyphenyl) triphenylboron, and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like).

Among these aryl borate compounds, it is more preferable to use a borate compound having 3 or 4 aryl groups in one molecule from the viewpoint of storage stability. Further, these aryl borate compounds can be used alone or as a mixture of two or more.

Examples of sulfur-containing reductive inorganic compound include sulfites, bisulfites, pyrosulfites, thiosulfates, thionates and dithionite. Specific examples include sodium sulfite, potassium sulfite, calcium sulfite, ammonium sulfite, sodium bisulfite, potassium bisulfite, 3-mercaptopropyl trimethoxysilane, 2-mercaptobenzoxazole, decanethiol, thiobenzoic acid and the like.

Examples of nitrogen-containing reductive inorganic compound include nitrites, and specific examples include sodium nitrite, potassium nitrite, calcium nitrite, ammonium nitrite and the like.

Specific examples of barbituric acid derivative include salts (alkali metals or alkaline earth metals are preferred) of barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl barbituric acid, 1,3-dimethyl-5-cyclopentyl barbituric acid, 1,3-dimethyl-5-cyclohexyl barbituric acid 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids. Specifically, the salts of these barbituric acids include sodium 5-butyl barbiturate, sodium 1,3,5-trimethyl barbiturate, sodium 1-cyclohexyl-5-ethyl barbiturate and the like.

Specific examples of the halogen compound include dilauryl dimethyl ammonium chloride, lauryl dimethyl benzyl ammonium chloride, benzyl trimethyl ammonium chloride, tetramethyl ammonium chloride, benzyl dimethyl acetyl ammonium chloride, dilauryl dimethyl ammonium bromide and the like.

The dental photocurable composition of the present disclosure comprises (D1) tertiary aliphatic amine compound having Log P of 2 or more and pKa of 10 or less as the (D) photopolymerization accelerator.

In the conventional dental photocurable composition containing a photoacid generator, a compound such as methyl diethanolamine, triethanolamine and dimethylamino ethylmethacrylate is used in the case of containing a tertiary aliphatic amine compound as the (D) photopolymerization accelerator. Good mechanical strength is exhibited by combining such an amine compound with a photosensitizer and a photoacid generator. However, it was confirmed that there is a case that gelation occurs in the case of storing a matrix containing a polymerizable monomer, a photoacid generator, and a tertiary aliphatic amine compound as the (D) photopolymerization accelerator, for a long period of time. In a preparation of a dental photocurable composition, a matrix is prepared by dissolving a photopolymerization initiator in a polymerizable monomer, and then mixed with a filler to prepare a paste-like dental photocurable composition. When the storage stability of the matrix is poor, the storage stability of the paste deteriorates in the case of taking a long time from the preparation of the matrix to the preparation of the paste. Therefore, there is a problem in preparation because of variation caused in physical properties of the dental photocurable composition and time constraint such that it is required to prepare a paste immediately after the preparation of a matrix. Thus, in order to improve the storage stability of the matrix, an attempt was made to increase a compounding amount of the polymerization inhibitor, which is a general method for suppressing gelation. However, for example, gelation does not occur by compounding 1 part by mass or more of the polymerization inhibitor with respect to 100 parts by mass of the (A) polymerizable monomer, but it has been confirmed that the curability tends to be significantly reduced, and the composition did not sufficiently function as a dental photocurable composition. As a result of some studies, it has been confirmed that the period until gelation occurs tends to be extended even when the polymerization inhibitor is not excessively compounded. However, satisfactory results have not been obtained with all the tertiary aliphatic amine compounds as the (D) polymerization accelerators. Furthermore, as a result of studies of various amine compounds, it has been confirmed that the storage stability of the matrix is improved by using a polymerizable monomer having an acidic group as the (A) polymerizable monomer and (D1) tertiary aliphatic amine compound having Log P of 2 or more and pKa of 10 or less as tertiary aliphatic amine compound which is used as the (D) polymerization accelerator, and the present disclosure has been completed.

The Log P in the present disclosure is an index indicating the hydrophobicity of the compound, and pKa is an index indicating the strength of the acid quantitatively. As a result of studies of various amine compounds, it has been found that the storage stability is good in the case of compounding a tertiary aliphatic amine compound having high hydrophobicity and higher acidity in the matrix. Although the detailed reason is unknown, it is assumed that because the photoacid generator is an acidic compound, acidity is low. Therefore, it is considered that when a tertiary aliphatic amine compound having high basicity is compounded, an acid-base reaction or the like is easily occurred to decrease the storage stability. Further, the lower the hydrophobicity, the weaker the degree of dissolution in the polymerizable monomer and/or the matrix, therefore it is considered that the matrix separation and gelation are easily occurred due to the partial presence of amine in a high concentration, to lower the storage stability. In the present disclosure, Log P and pKa are calculated using ChemDraw Professional ver 20.0. For compounds having a hydroxy group, the pKa of the hydroxy group was excluded, and pKa derived from an amine was used. For compounds having two or more N atoms, higher pKa values were used.

Preferable examples of specific examples of the (D1) tertiary aliphatic amine compound having Log P of 2 or more and pKa of 10 or less are roughly divided into those having a saturated heterocyclic structure, those having an aryl group, those having a dialkylamino group, and those having a hydroxy group. Examples of the saturated heterocyclic compound include 1,2,2,6,6-pentamethyl-4-piperidyl methacrylate which is an ester reactant of 4-hydroxy-1,2,2,6,6-pentamethyl piperidine and (meth) acrylic acid and the like and 2-((((1,2,2,6,6-pentamethyl piperidine-4-yl) oxy) carbonyl) amino) ethoxy) ethyl methacrylate which is a reactant of 4-hydroxy-1,2,2,6,6-pentamethyl piperidine with isocyanate such as 2-isosyanatoethyl methacrylate and 2-(2-methacryloyl oxyethyloxy) ethyl isocyanate. In addition, examples of the compound having an aryl group include 1-[(3,3-diphenylpropyl) (methyl) amino]-2-methyl-2-propanol, and among the aryl groups, the benzyl group is preferable because it is more general. Among them, those having a dibenzylamino structure can be preferably used. Examples include, tribenzylamine, dibenzyl glycineethyl, dibenzyl methylamine, dibenzyl ethanolamine, dibenzyl aminopropanolamine and the like. Further, examples include 3-(dibenzylamino) ethyl (meth) acrylate, 3-(dibenzylamino) propyl (meth) acrylate and the like, which are ester reaction products of dibenzyl alcohol amines and (meth) acrylic acid. In addition, examples include 2-benzyl-6-oxo-1-phenyl-5,10-dioxo-2,7-diazadodecane-12-yl methacrylate, which is a reaction product of dibenzyl alcohol amines with isocyanates such as 2-isocyanatoethyl methacrylate and 2-(2-methacryloyloxy ethyloxy) ethyl isocyanate. Furthermore, examples of those having a dialkylamino group include N,N-diisopropyl aminoethyl methacrylate, which is an ester reaction product of a dialkylamino alcohol and (meth) acrylic acid, and 3-isopropyl-2-methyl-7-oxo-6,11-dioxa-3,8-diazatridecane-13-ylmethacrylate and 2-(((2-(diisopropylamino) ethoxy) carbonyl) amino) ethyl methacrylate and the like which are reaction products with dialkylaminoalcohol and isocyanate such as 2-isocyanatoethyl methacrylate and 2-(2-methacryloyloxy ethyloxy) ethyl isocyanate. In addition, examples of the compound having a hydroxy group include stearyldiethanolamine and lauryldiethanolamine.

Among the above-described (D1) tertiary aliphatic amine compound having Log P of 2 or more and pKa of 10 or less, compounds having a polymerizable group are more preferable. Since such a tertiary aliphatic amine compound can be copolymerized with the (A) polymerizable monomer in the dental photocurable composition, it can be expected that the risk of elution of unreacted substances is reduced.

Formula (2) shows an example of a specific structure of a compound having a polymerizable group and having a saturated heterocyclic structure.

[Formula (2)]

[Chemical formula 1]

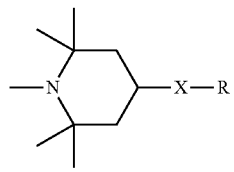

(In the formula, X is an ester bond or a urethane bond, and R is an organic group having a radically polymerizable group.)

Formula (3) shows an example of a specific structure of a compound having a polymerizable group and having an aryl group.

[Formula (3)]

[Chemical formula 2]

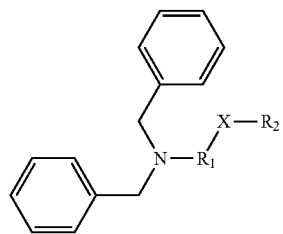

(In the formula, $R_1$ is a hydrocarbon group having 2 to 3 carbon atoms, X is an ester bond or a urethane bond, and $R_2$ is an organic group having a radically polymerizable group.)

Formula (4) shows an example of a specific structure of a compound having a polymerizable group and having a dialkylamino group.

[Formula (4)]

[Chemical formula 3]

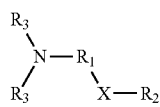

(In the formula, $R_1$ is a hydrocarbon group having 2 to 3 carbon atoms, X is an ester bond or a urethane bond, $R_2$ is an organic group having a radically polymerizable group, and $R_3$ is a hydrocarbon group having 3 or more carbon atoms.)

Examples having the structure of the formula (2) include 1,2,2,6,6-pentamethyl-4-piperidyl methacrylate and 2-((((1,2,2,6,6-pentamethyl piperidine-4-yl) oxy) carbonyl) amino) ethoxy) ethyl methacrylate. Examples having the structure of the formula (3) include 3-(dibenzylamino) ethyl (meth) acrylate, 3-(dibenzylamino) propyl (meth) acrylate and 2-(2-methacryloyloxy ethyloxy) ethylisocyanate. Examples having the structure of the formula (4) include N,N-diisopropyl aminoethyl methacrylate and 3-isopropyl-2-methyl-7-oxo-6,11-dioxa-3,8-diazatridecane-13-ylmethacrylate.

As a typical structural tendency in the (D1) tertiary aliphatic amine compound having Log P of 2 or more and pKa of 10 or less, an electron-withdrawing group is bonded to α-carbon, ß-carbon and γ-carbon bonded to N atom derived from an amine. Specific examples of the electron-withdrawing group include a hydroxy group, an aryl group, an ester bond and a urethane bond, and among these, those containing an aryl group and/or an ester bond and/or a urethane bond are preferable. There is a tendency to reduce pKa by having an electron-withdrawing group. Further, a saturated heterocyclic compound or a compound to which an aryl group is bonded is preferable because there is a tendency to improve Log P. In addition, it is not preferable that an amino group, a nitro group or a primary hydroxy group is contained at α-carbon and/or ß-carbon bonded to the N atom derived from an amine, because the cured body has a strong yellowish and low aesthetic property and discoloration is caused in the case of storing for a long period of time. In the present disclosure, the α-carbon means the first carbon adjacent to N atom derived from an amine, the ß-carbon means the second carbon next to the first carbon, and the γ-carbon means the third carbon next to the second carbon. When the primary hydroxy group is bonded to a carbon other than α-carbon and/or ß-carbon starting from N atom, there is a case that it does not cause discoloration. In the present disclosure, the N atom derived from an amine means N atom which is bonded with a hydrogen atom or a hydrocarbon group. For example, it is distinguished from N atom derived from an amide bond, a urethane bond, a urea bond, an azo group, and a nitro group.

The dental photocurable composition of the present disclosure may not substantially comprise a tertiary aliphatic amine compound having Log P of less than 2 or pKa of more than 10. The term "not substantially comprise" includes the case where an amount less than 0.1 parts by mass, preferably less than 0.01 parts by mass is contained in 100 parts by mass of the polymerizable monomer. However, this does not apply in the case of containing as an impurity in the raw material and not affecting the physical properties. When 0.1 part by mass or more of the tertiary aliphatic amine compound having Log P of less than 2 or pKa of more than 10 is contained, there is a case where the storage stability of the matrix decreases. In addition, the dental photocurable composition of the present disclosure may not comprise a tertiary aliphatic amine compound having Log P of less than 2 or pKa of more than 10.

It is not preferable that the dental photocurable composition of the present disclosure contains an amine compound having two or more primary hydroxy groups at α-carbon and/or ß-carbon starting from N atom derived from an amine. Further, it is not preferable that the dental photocurable composition of the present disclosure contains an amine compound having a primary hydroxy group at α-carbon and/or ß-carbon starting from N atom derived from an amine contains. When such an amine compound is contained, there is a case that the cured product of the dental photocurable composition is discolored with over time. Therefore, the dental photocurable composition of the present disclosure may not substantially comprise a tertiary aliphatic amine compound having two or more primary hydroxy groups at α-carbon and/or ß-carbon starting from N atom derived from an amine. The term "not substantially comprise" includes the case where an amount less than 0.1 parts by mass, preferably less than 0.01 parts by mass is contained in 100 parts by mass of the polymerizable monomer. However, this does not apply in the case of containing as an impurity in the raw material and not affecting the physical properties. In addition, the dental photocurable composition of the present disclosure may not comprise a tertiary aliphatic amine compound having two or more primary hydroxy groups at α-carbon and/or ß-carbon starting from N atom derived from an amine.

The dental photocurable composition of the present disclosure may not substantially comprise an aromatic amine compound. The term "not substantially comprise" includes the case where an amount less than 0.1 parts by mass, preferably less than 0.01 parts by mass is contained in 100 parts by mass of the polymerizable monomer. However, this does not apply in the case of containing as an impurity in the raw material and not affecting the physical properties. In addition, the dental photocurable composition of the present disclosure may not comprise an aromatic amine compound. When an aromatic amine compound is contained, there is a case that discoloration occurs in the case of exposing light for a long period of time. On the other hand, since discoloration due to light exposure can be suppressed by compounding an ultraviolet absorber. Therefore, when an ultraviolet absorber is compounded, there may be no major problem in discoloration of the cured body even if an aromatic amine compound is compounded.

There is no problem even if these (B) photosensitizers, (C) photoacid generators and (D) photopolymerization accelerators, which are polymerization initiators, are subjected to a secondary treatment such as finely pulverization, adsorption on a carrier and encapsulation in a microcapsule, if necessary. Furthermore, these photo polymerization initiators can be used not only singly but also in combinations of two or more, regardless of the polymerization manner or the polymerization method.

The compounding amount of the (D) photopolymerization accelerator is preferably 0.2 to 10 parts by mass, more preferably 0.5 to 10 parts by mass, with respect to 100 parts by mass of the total amount of the (A) polymerizable monomer contained in the dental photocurable composition. When the compounding amount is less than 0.2 parts by mass, there is a case where the mechanical strength is insufficient. When the compounding amount is more than 10 parts by mass, although it has sufficient curability, the sensitivity to light is shortened, and discoloration such as browning or yellowing of the cured body may increase, and therefore it is not preferable.

The compounding amount of the (D1) tertiary aliphatic amine compound having Log P of 2 or more and pKa of 10 or less is preferably 0.2 to 5 parts by mass, more preferably 0.5 to 50 parts by mass, with respect to 100 parts by mass of the total amount of the (A) polymerizable monomer contained in the dental photocurable composition. When the compounding amount is less than 0.2 parts by mass, there is a case where the mechanical strength is insufficient. When the compounding amount is more than 5 parts by mass, although it has sufficient curability, the sensitivity to light is shortened, and discoloration such as browning or yellowing of the cured body may increase, and therefore it is not preferable.

The dental photocurable composition of the present disclosure may comprise only the (D1) tertiary aliphatic amine compound having Log P of 2 or more and pKa of 10 or less as the (D) photopolymerization accelerator. Further, the dental photocurable composition of the present disclosure may comprise only the (D1) tertiary aliphatic amine compound having Log P of 2 or more and pKa of 10 or less as the (D) photopolymerization accelerator, and the (D1) tertiary aliphatic amine compound having Log P of 2 or more and pKa of 10 or less may be a compound that an electron-withdrawing group is bonded to any one of more of α-carbon, ß-carbon and γ-carbon bonded to N atom derived from an amine and the electron-withdrawing group is selected from an aryl group, an ester bond and/or an urethane bond. Specific examples of such compounds include 1,2,2,6,6-pentamethyl-4-piperidyl methacrylate, 2-((((1,2,2,6,6-pentamethyl piperidine-4-yl) oxy) carbonyl) amino) ethoxy) ethyl methacrylate, 1-[(3,3-diphenylpropyl) (methyl) amino]-2-methyl-2-propanol, tribenzylamine, dibenzylglycine ethyl, dibenzylmethyl amine, dibenzylethanol amine, dibenzylamino propanolamine, 3-(dibenzylamino) ethyl (meth) acrylate, 3-(dibenzylamino) propyl (meth) acrylate, 2-benzyl-6-oxo-1-phenyl-5,10-dioxo-2,7-diazadodecane-12-yl methacrylate, N,N-diisopropyl aminoethyl methacrylate, 3-isopropyl-2-methyl-7-oxo-6,11-dioxa-3,8-diazatridecane-13-ylmethacrylate and 2-(((2-(diisopropylamino) ethoxy) carbonyl) amino) ethyl methacrylate and the like.

[(E) Filler]

The dental photocurable composition of the present disclosure contains (E) filler. As the (E) filler used in the present disclosure, a known filler commonly used can be used without any limitation.

The type of the (E) filler is not limited as long as it is a known filler, and a filler suitable for the application can be compounded, and it is preferable that a filler such as an inorganic filler, an organic filler, an organic-inorganic composite filler and an ion sustained release glass is compounded. In the dental photocurable composition of the present disclosure, the filler described in the specific example may be used alone, or two or more kinds of fillers may be used in combination.

As the inorganic filler, the chemical composition is not particularly limited, but specific examples include silicon dioxide, alumina, titania, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass and the like. Particularly, barium fluoroaluminosilicate glass, strontium fluoroaluminosilicate glass, fluoroaluminosilicate glass and the like, which are used in dental glass ionomer cement, resin reinforced glass ionomer cement and resin cement and the like, can also be suitably used. The fluoroaluminosilicate glass as used herein has a basic structure of silicon oxide and aluminum oxide and contains an alkali metal for introducing non-crosslinked oxygen. The fluoroaluminosilicate glass further has an alkaline earth metal including strontium and fluorine as modified/coordinated ions. The fluoroaluminosilicate glass may be also a composition in which a lanthanoid series element is incorporated into the skeleton in order to impart further radiopacity. This lanthanoid series element also participates in the composition as a modified/coordinated ion.

As the inorganic filler, a hydrophobized inorganic fine particle may be contained. The average particle diameter of the primary particles of the hydrophobic inorganic fine particle is preferably 0.1 to 50 nm, and the hydrophobization is preferably treated with a silane coupling agent and/or a modified silicone oil. By compounding, it can be expected to suppress the sedimentation of the inorganic filler and impart rheological characteristics in addition to improving the flexural strength.

Specific examples of the organic filler include polymers such as polymethyl methacrylate, polyethyl methacrylate, methyl methacrylate-ethyl methacrylate copolymer, ethyl methacrylate-butyl methacrylate copolymer, methyl methacrylate-trimethylolpropane methacrylate copolymer, polyvinylchloride, polystyrene, chlorinated polyethylene, nylon, polysulfone, polyethersulfone and polycarbonate.

Specific examples of the organic/inorganic composite filler include one obtained by covering the surface of a filler with a polymerizable monomer by polymerization, one obtained by mixing a filler and a polymerization monomer and polymerizing the monomer and thereafter grinding the resultant to a proper particle size, one obtained by dispersing a filler in a polymerizable monomer in advance for emulsion polymerization or suspension polymerization, one obtained by spray-drying a polymerizable monomer and a solvent which are dispersed with a filler in advance and polymerizing, and one obtained by spray-drying a solvent which is dispersed with a filler in advance, impregnating a polymerizable monomer and polymerizing, but are not limited thereto at all.

The feature of the ion sustained release glass is that at least one of fluorine ion, strontium ion, borate ion and aluminum ion is sustained release. Among these ions, it is preferable that a plurality of these ions are released at the same time.

As the ion sustained release glass used in the present disclosure, any ion sustained release glass can be used without any limitation as long as such ion sustained release glass includes one or more kinds of glass skeleton forming elements which form a glass skeleton, and one or more kinds of glass modifying elements which modify the glass skeleton. These ion sustained release glasses may be used alone or in combination of two or more thereof. Further, in the present disclosure, glass amphoteric elements that play a role of either a glass skeleton forming element or a glass modifying element depending on the glass composition are included within a category of a glass skeleton forming element. Specific examples of the glass skeleton forming element contained in the ion sustained release glass, include silica, aluminum, boron and phosphorus, and these can be used not only singly but also in combinations of a plurality thereof. Specific examples of the glass modifying element include halogen elements such as fluorine, bromine and iodine, alkali metal elements such as sodium and lithium, and alkali earth metal elements such as calcium and strontium, and these can be used not only singly but also in combinations of a plurality thereof. Among them, a glass composition including silica, aluminum or boron as the glass skeleton forming element and including fluorine, sodium or strontium as the glass modifying element is preferable, and specific examples include a silica glass, a fluoroaluminosilicate glass, a fluoroborosilicate glass and a fluoroalumino borosilicate glass containing strontium or sodium. Furthermore, from the viewpoint of sustainably releasing fluorine ion, strontium ion, borate ion or aluminum ion, a fluoroalumino borosilicate glass containing strontium is more preferable. Example of the glass composition range thereof is as follows: $SiO_2$: 15 to 35% by mass, $Al_2O_3$: 15 to 30% by mass, $B_2O_3$: 5 to 20% by mass, SrO: 20 to 45% by mass, F: 5 to 15% by mass, and $Na_2O$: 0 to 10% by mass. The glass composition can be confirmed by using an instrumental analysis such as an elementary analysis, Raman spectrum, and fluorescence X-ray analysis, and there is no problem as long as the actual measurement by any analysis methods matches to these composition ranges.

A method for preparing an ion sustained release glass is not particularly limited, and the glass can be produced by a preparing method such as a melting method or a sol-gel method. Among them, a preparing method by a melting method using a melting furnace is preferable from the viewpoint of ease of design of the glass composition, including raw material selection. The ion sustained release glass used in the present disclosure has an amorphous structure, but there is no problem even if it contains a partially crystalline structure, and further, a mixture of a glass having an amorphous structure and a glass having a crystal structure may be used without any problem. Whether the structure of the glass is an amorphous structure can be confirmed using an X-ray diffraction analysis or an analysis instrument such as a transmission electron microscope. In particular, the ion sustained release glass used in the present disclosure sustainably releases various ions by means of an equilibrium relation with ion concentrations in the external environment, and therefore an amorphous structure which is a homogeneous structure is preferable.

Further, in order to enhance ion sustained release property of the ion sustained release glass, it is preferable embodiment to functionalize the glass surface by a surface treatment, thereby improving the ion sustained-release property. Specific examples of a surface treatment material used in the surface treatment include a surfactant, a fatty acid, an organic acid, an inorganic acid, a monomer, a polymer, various coupling materials, a silane compound, a metal alkoxide compound, and a partially condensed product thereof. Among these surface treatment materials, it is preferable to perform composite surface treatment using an acidic polymer and a silane compound.

The composite surface treatment is a method for surface treatment by using an acidic polymer after coating the surface of the ion sustained release glass with a silane compound. Specific example is described in the following. A silane compound represented by the formula (5) is mixed in an aqueous dispersion containing an ion sustained release glass finely pulverized to a desired average particle diameter (D50) by pulverization or the like. The mixture is hydrolyzed or partially hydrolyzed in the system to prepare a silanol compound. Then the silanol compound is condensed to form a polysiloxane, and then the surface of the ion sustained release glass is coated with the polysiloxane to obtain a polysiloxane coated ion sustained release glass.

[Formula (5)]

[Chemical formula 4]

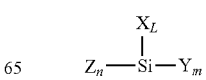

(in the formula, Z is RO—, X is halogen, Y is OH—, R is an organic group whose carbon number is less than or equal to 8, and n, m, and L are each an integer from 0 to 4 where n+m+L=4)

Specific Examples of the silane compound represented by the formula (3) include tetramethoxysilane, tetraethoxysilane, tetrapropoxysilane, tetraallyloxysilane, tetrabutoxysilane, tetrakis (2-ethylhexyloxy) silane, trimethoxychlorosilane, triethoxychlorosilane, triisopropoxychlorosilane, trimethoxyhydroxysilane, diethoxydichlorosilane, tetraphenoxysilane, tetrachlorosilane and silicon hydroxide (silicon oxide hydrate), more preferable include tetramethoxysilane and tetraethoxysilane.

A low condensed product of the silane compound represented by the formula (3) is more preferable. Examples include a low condensed silane compound obtained by partial hydrolysis and condensation of tetramethoxysilane and tetraethoxysilane. These compounds can be used singly or in combination. An organosilane compound can also be added in the polysiloxane treatment as a part of the silane compound represented by the formula (5).

The polysiloxane coated ion sustained release glass, obtained in the above step, can be subjected to an acidic polymer treatment for a reaction with an acidic polymer to thereby provide an ion sustained release glass. The acidic polymer treatment can be conducted by using an equipment commonly used in the art as long as the equipment is a dry fluid type stirring machine, and examples include a Henschel mixer, a super mixer and a high-speed mixer. The reaction of the ion sustained release glass formed with the polysiloxane film and an acidic polymer can be conducted by contacting an acidic polymer solution by impregnating, spraying or the like. As an example, it is only necessary to perform a dry fluid of the polysiloxane coated ion sustained release glass, dispersing the acid polymer solution from above in the flow state, and sufficiently stirring. The method for dispersing the acidic polymer solution is not particularly limited, and a dropping or spraying method that can uniformly disperse is more preferable. The reaction is preferably conducted around room temperature, and when the temperature increases, there is a case that the reaction of an acid reactive element and the acidic polymer is fast, and thereby formation of an acidic polymer layer is not uniform.

It is preferable to remove the water content in the cement reaction phase by performing a heat treatment after the reaction. If water content remains in the cement reaction phase, it is disadvantageous in terms of strength, but since the filler of the present disclosure is covered and strengthened by the coupling agent condensate film, the decrease in mechanical strength is suppressed. The heat treatment method after the acid polymer treatment is not particularly limited, and can be performed by a known general method. As the equipment used for the heat treatment, a box-type hot air dryer or the like, a rotary heat treatment device capable of uniform heating and the like are preferable. The heat treatment temperature is in the range from room temperature to 200° C., more preferably in the range from 40 to 150° C. When the temperature is lower than this range, there is a risk that the removal of the aqueous medium is insufficient, and when the temperature is higher than this range, there is a risk that the organic layer of the acidic polymer is decomposed or discolored. Since the heat treatment period depends on the capacity of the dryer and the like, there is no problem as long as the aqueous medium can be sufficiently removed. After a heat treatment, a heat-treated product can be easily deagglomerated by application of a shear force or an impact force, and the deagglomerating method can be performed by, for example, the equipment used in the above reaction.

A solvent used for preparing the acid polymer solution used for the reaction may be solvent which dissolves the acid polymer without any problems. Examples of the solvent include water, ethanol, and acetone. Of these, water is particularly preferable. When water is used, an acid group of the acid polymer dissociates and reacts uniformly with the surface of polysiloxane-coated inorganic filler which acts as a core.

The weight average molecular weight of the polymer dissolved in the acid polymer solution is in the range of 2000 to 50000, and preferably in the range of 5000 to 40000. In the case of treating with the acidic polymer having a weight average molecular weight of less than 2000, there is a tendency that an acidic polymer reaction phase is not formed in the ion sustained release glass, and as a result, the ion sustained release property is low. On the other hand, in the case of treating with an acidic polymer having a weight average molecular weight of more than 50000, the viscosity of the acidic polymer solution becomes high, and therefore it may be difficult to uniformly treat the polysiloxane coated ion sustained release glass. The concentration of the acidic polymer in the acidic polymer solution is preferably in the range from 3 to 25% by mass, more preferably in the range from 8 to 20% by mass. When the concentration of the acidic polymer is less than 3% by mass, the above described acidic polymer reaction phase is brittle and therefore the effect of improving the sustained release of ions cannot be obtained. When the concentration of the acidic polymer is more than 25% by mass, the polysiloxane layer (porous) is difficult to diffuse in a uniform state, a homogeneous acidic polymer reaction phase is not obtained, and the reaction occurs immediately after contact with the polysiloxane coated ion sustained release glass, and therefore there is a problem that strongly reacted agglomerates generates. The addition amount of the acidic polymer solution to the polysiloxane coated ion sustained release glass is preferably in the range from 6 to 40% by mass, more preferably 10 to 30% by mass. Converting in this addition amount, an optimal amount of the acid polymer with respect to the polysiloxane coated ion sustained release glass is in the range of 1 to 7% by mass, and an optimal amount of water is in the range of 10 to 25% by mass.

As the acid polymer that can be used to form the acid polymer reaction phase on the surface of the polysiloxane coated ion sustained release glass by the method described above, any copolymers or homopolymers as long as the copolymer or homopolymer is a copolymer or homopolymer of a polymerizable monomer having an acid group such as a phosphoric acid residue, a pyrophosphoric acid residue, a thiophosphoric acid residue, a carboxylic acid residue, or a sulfonic acid residue. Specific examples of these polymerizable monomers include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meta) acryloyloxy ethoxycarbonyl phthalic acid, 4-(meta) acryloyloxy ethoxycarbonyl phthalic anhydride, 5-(meta) acryloylamino pentylcarboxylic acid, 11-(meth) acryloyloxy-1,1-undecane dicarboxylic acid, 2-(meta) acryloyloxyethyl dihydrogen phosphate, 10-(meta) acryloyloxydecyl dihydrogen phosphate, 20-(meta) acryloyloxyeicosil dihydrogen phosphate, 1,3-di (meth) acryloyloxypropyl-2-dihydrogen phosphate, 2-(meta) acryloyloxyethyl phenyl phosphate, 2-(meta) acryloyloxyethyl-2'-bromoethyl phosphate, (meta) acryloyloxyethyl phenylphosphonate, [2-(meth) acryloyloxyethyl] pyrophosphate, 2-(meta) acryloyloxyethyl dihydrogen dithiophosphate and 10-(meta) acryloyloxydecyl dihydrogen thiophosphate. Of these polymers which are (co) polymer of these polymerizable monomers, a homopolymer or a copolymer of α-ß unsaturated carboxylic acid that is relatively slow in acid-base reaction with an acid reactive element contained in the polysiloxane coated ion sustained release glass is preferable, and specific examples include an acrylic acid polymer, an acrylic acid-maleic acid copolymer, and an acrylic acid-itaconic acid copolymer.

The above described (E) filler can be treated with a surface treatment material represented by a silane coupling material in order to improve the affinity to the polymerizable monomer, the dispersability in the polymerizable monomer, and the mechanical strength and water resistance of the cured product. The surface treatment material and the surface treatment method are not particularly limited, and known methods such as a method of spraying the surface treatment material while stirring the powdery filler, a method of dispersing and mixing the filler and the surface treatment material in a solvent, and a method of supplying a vapor or gaseous silane coupling material to the filler surface, can be adopted without limitation. As a silane coupling material used for surface treatment of the filler, methyltrimethoxysilane, methyltriethoxysilane, methyltrichlorosilane, dimethyldichlorosilane, trimethylchlorosilane, vinyltrichlorosilane, vinyltriethoxysilane, vinyltris (2-methoxyethoxy) silane, 3-methacryloyloxypropyl trimethoxysilane, 3-chloropropyl trimethoxysilane, 3-glycidoxypropyl trimethoxysilane, 3-(meth) acryloxypropyl trimethoxysilane, 8-(meth) acryloxyoctyl trimethoxysilane, 11-(meth) acryloxiundecyl trimethoxysilane, hexamethyldisilazane and the like are preferable. In addition to the silane coupling material, surface treatment of the filler can be performed by a method using a titanate coupling material or an aluminate coupling material. The treatment amount of the surface treatment material in the filler is preferably 0.01 to 30 parts by mass, more preferably 0.5 to 20 parts by mass with respect to 100 parts by mass of the filler before treatment.

The shape of the (E) filler is not particularly limited, and any shape of the filler such as a spherical shape, a needle shape, a plate shape, a crushed shape or a scale shape can be used. The average particle diameter of the filler is preferably 0.01 μm to 50 μm, more preferably 0.01 μm to 30 μm, still more preferably 0.05 μm to 20 μm, and more preferably 0.05 μm to 10 μm.

It is preferable that the dental photocurable composition of the present disclosure contains 1 to 500 parts by mass of the (E) filler with respect to 100 parts by mass of the (A) polymerizable monomer contained in the matrix. When the compounding amount is less than 1 part by mass, there is a case that the storage stability is deteriorated or the operability is poor. When the compounding amount is more than 500 parts by mass, there is a case that the operability of the dental photocurable composition is deteriorated.

The dental photocurable composition of the present disclosure preferably contains a hydrophobic silica fine particle having an average particle diameter of the primary particles of 1 to 40 nm as the (E) filler in order to impart rheological property. The primary particle diameter indicates the diameter of one particle (primary particle) constituting the powder. In the present disclosure, the average particle diameter may be, for example, an average particle diameter calculated based on a volume-based grain size distribution measured by a laser diffraction type particle size distribution measuring device or the like, and may be measured by, for example, a laser diffraction type grain size measuring apparatus (Microtrac MT3300EXII: NIKKISO Co., Ltd.). In addition, the primary particle diameter can be measured by dynamic light scattering particle size measurement and can be measured by using electron micrographs for the case that primary particles are strongly aggregated to form secondary particles. It is preferably that the average particle diameter of the primary particles of the silica fine particle is 1 to 40 nm. Examples of a method for hydrophobizing a silica fine particle include surface treatment with a modified silicone oil such as dimethylsilicone oil and/or surface treatment with a silane coupling material which has an alkylsilyl group and may have a trimethylsilyl group, a dimethylsilyl group, a methylsilyl group or a (meth) acryloyl group having an alkyl chain having 3 or more and 18 or less carbon atoms.

Specific examples of the hydrophobic silica fine particle include Aerosil R972, Aerosil R974, Aerosil R976, Aerosil R711, Aerosil R7200, Aerosil R976S, Aerosil R202, Aerosil R812, Aerosil R812S, Aerosil R805, Aerosil R8200, Aerosil R104, Aerosil R106, Aerosil RY200, Aerosil RX200, Aerosil RY200S, Aerosil RA200H and Aerosil RA200HS, which are manufactured by Nippon Aerosil Co., Ltd. and commercially available under the trade name of Aerosil.

By containing the hydrophobic silica fine particle having an average particle diameter of the primary particles of 1 to 40 nm, the dental photocurable composition exhibits appropriate thixotropy and thus has good operability. In the dental photocurable composition of the present disclosure, since the matrix itself exhibits good storage stability, good storage stability can be expected even if the compounding amount of the filler in the dental photocurable composition is small. Generally, when the compounding amount of the filler is large, there is a case that the transparency is lowered and the elasticity and the flexibility is lowered. There is a case that transparency, elasticity and flexibility are required in a dental coating material, a dental lining material, a dental cement, a dental bonding material, a dental splinting material and a dental manicure material. When the compounding amount of the filler in the dental photocurable composition is reduced in order to avoid such a case, there is a case that the operability is deteriorated. In such a case, the hydrophobic silica fine particle having an average particle diameter of the primary particles of 1 to 40 nm is preferably used because it is expected to impart rheological property and to improve operability by small compounding amount. It is preferable that the dental photocurable composition of the present disclosure contains 1 to 30 parts by mass of the hydrophobic silica fine particle having an average particle diameter of the primary particles of 1 to 40 nm with respect to 100 parts by mass of the (A) polymerizable monomer contained in the matrix. When the compounding amount is less than 1 part by mass, there is a case that the rheological property is not exhibited. When the compounding amount is more than 30 parts by mass, there is a case that the operability of the dental photocurable composition is deteriorated.

The matrix in the present disclosure refers to a medium having a lower viscosity than a paste containing a polymerizable monomer, a photosensitizer, a photoacid generator, a photopolymerization accelerator and a filler. In order to uniformly disperse the photopolymerization initiator in the paste by dissolving the photopolymerization initiator such as a photosensitizer, a photoacid generator or a tertiary aliphatic amine compound in the polymerizable monomer, the paste is prepared by mixing the matrix and the filler after preparing the matrix. In particular, solids at room temperature may cause sedimentation and performance variation in the case of not be dissolved in the matrix. In the case of dispersing uniformly without sedimentation in the matrix, a filler having the primary particles diameter exceeding 100 nm may be compounded after compounding a filler having the primary particles diameter of 100 nm or less. Since it is preferable to contain a process for confirming that the matrix has been dissolved in manufacturing, it is preferable that the matrix does not contain a filler that does not dissolve in the matrix.

In the present disclosure, a paste is prepared by compounding a polymerizable monomer, a photosensitizer, a photoacid generator and a photopolymerization in a matrix, sufficiently mixing, and then mixing with a filler. Therefore, since the matrix and the paste are prepared on different days, the storage stability of the matrix alone is required. When the storage stability of the matrix is poor, there is a difference in physical property between the dental photocurable composition prepared on the next day of preparing the matrix and the dental photocurable composition prepared after storing the matrix for a certain period of time from preparing the matrix. In particular, there is a case that the physical property of the dental photocurable composition prepared after storing the matrix for a certain period of time after preparing the matrix, and there is a case that the dental photocurable composition cannot be prepared due to gelation of the matrix itself. Although there is a method of quickly preparing a paste on the next day of preparing the matrix, handling becomes complicated by setting an extremely short matrix expiration date. For this reason, it is preferable to have a certain period of time until expiration date of use of the matrix. In the present disclosure, an evaluation is set to good in the case that the matrix stored at 50° C. for 2 weeks does not gel and the dental photocurable composition prepared with the matrix stored at 50° C. for 2 weeks exhibits a certain level or more of physical property.

Comparing the matrix and paste, the matrix state is less in storage stability and gelation is more likely to occur. Although the detailed cause is unknown, it is considered that the concentration of the polymerizable monomer in the composition is reduced by compounding the (E) filler and therefore the collision probability between the polymerizable monomers is reduced. For this reason, it is preferable that the compounding amount of the (E) filler is large in terms of the storage stability of the paste. The preferable compounding amount of the filler (E) is 1 part by mass or more of the (E) filler with respect to 100 parts by mass of the (A) polymerizable monomer contained in the matrix, and is 100 parts by mass in the case that high mechanical strength is required. In particular, the elastic modulus tends to increase as the compounding amount of the (E) filler increases. On the other hand, when the compounding amount of the filler (E) is more than 500 parts by mass, there is a case that the operability of the dental photocurable composition is deteriorated. However, in dental practice, several types of materials have been developed to accommodate various cases. In particular, in material that flexibility and toughness is required rather than mechanical strength, there is a case that the compounding amount of the filler is 30 parts by mass or less with respect to 100 parts by mass of the (A) polymerizable monomer contained in the matrix. Examples of such materials include a dental coating material, a dental lining material, a dental cement, a dental bonding material, a dental splinting material and a dental manicure material. In the matrix which is contained in the dental photocurable composition and contains (A) polymerizable monomer and (A1) polymerizable monomer having an acidic group, (B) photosensitizer, (C) photoacid generator, (D) photopolymerization accelerator and (D1) tertiary aliphatic amine compound having a Log P of 2 or more and pKa of 10 or less, high storage stability is exhibited by the matrix itself and therefore good storage stability can be expected for a material having 30 parts by mass or less with respect to 100 parts by mass of the (A) polymerizable monomer contained in the matrix.

The dental photocurable composition of the present disclosure may contain 1 to 30 parts by mass of the (E) filler with respect to 100 parts by mass of the (A) polymerizable monomer contained in the matrix. A preferred example of such a dental photocurable composition is a dental splinting material. Since the dental splinting material is an adhesive material used for fixing a mobile tooth due to gingival retraction or external wound, it requires appropriate flexibility rather than high strength. Therefore, the compounding amount of the (E) filler is smaller than that of a general dental photocurable composition. However, if it is not sufficiently cured, appropriate flexibility is not exhibited and the cured product becomes fragile. Therefore, the photopolymerization initiator is required to have excellent curability. Therefore, since high storage stability can be expected for a dental photocurable composition having a composition close to that of a matrix in which the compounding amount of the filler (E) is small, the dental photocurable composition is preferably used as a dental splinting material.

When the dental photocurable composition of the present disclosure is used as a dental splinting material, it is preferable that the dental photocurable composition contains a matrix containing (A) polymerizable monomer and (A1) polymerizable monomer having an acidic group, (B) photosensitizer, (C) photoacid generator and (D1) tertiary aliphatic amine compound having Log P of 2 or more and pKa of 10 or less and (E) filler, and the compounding amount of the (E) filler is 1 to 30 parts by mass with respect to 100 parts by mass of the (A) polymerizable monomer contained in the matrix. When the compounding amount of the filler (E) is less than 1 part by mass with respect to 100 parts by mass of the (A) polymerizable monomer contained in the matrix, there is a case that dripping of the dental photocurable composition easily occurs and therefore the operability is poor. On the other hand, when the compounding amount of the (E) filler exceeds 30 parts by mass with respect to 100 parts by mass of the (A) polymerizable monomer contained in the matrix, there is a case that the flexibility of the dental photocurable composition is lowered and therefore it is not preferable.

Other Component

Further, the dental photocurable composition of the present disclosure may contain a component other than above described (A) to (E) components within a range not to impair the effect of the present disclosure. For example, an excipient typified by fumed silica, benzophenone-based and benzotriazole-based ultraviolet absorbers, polymerization inhibitors such as hydroquinone, hydroquinone monomethyl ether and 2,5-ditershally butyl-4-methylphenol, chain transfer materials such as α-alkylstyrene compound, mercaptan compound such as n-butyl mercaptan and n-octyl mercaptan, and terpenoid compound such as limonene, myrsen, α-terpinene, ß-terpinene, γ-terpinene, terpinoren, ß-pinene and α-pinene, metal supplementary material such as aminocarboxylic acid chelating agent and phosphonic acid chelating agent, discoloration inhibitors, antibacterial materials, coloring pigments, water and solvent that can be mixed with water in any ratio, and other additives conventionally known in the art may be added as necessary and as desired.

A preparing method of the dental photocurable composition of the present disclosure is not particularly limited. Examples of a general preparing method of a dental photocurable composition include a method which comprises preparing a matrix by mixing (A) polymerizable monomer, (B) photosensitizer, (C) photoacid generator and (D) photopolymerization accelerator in advance, kneading the matrix and (E) filler, and removing air bubbles under reduced pressure to prepare a uniform paste. In the present disclosure, it can be prepared by the above-described method without any problem.

It is preferable that the dental photocurable composition of the present disclosure is used for a dental adhesive material, a dental composite resin, a dental core build-up material, a dental resin cement, a dental coating material, a dental sealant material, a dental manicure material, a dental splinting material, a dental CAD-CAM restoration material and a dental 3D printer material, it is particularly preferable to use for a dental adhesive material, a dental composite resin, a dental core build-up material, a dental resin cement, a dental coating material, a dental sealant material, a dental manicure material and a dental splinting material.

The dental photocurable composition of the present disclosure may contain only (A) polymerizable monomer, (B) photosensitizer, (C) photoacid generator, (D) photopolymerization accelerator and (E) filler. Further, as the components other than (A) to (E), only one or more of the above-mentioned components may be contained.

EXAMPLE

Hereinafter, example of the present disclosure are specifically described. However, the present disclosure is not intended to be limited to these Examples.

The materials used in Examples and Comparative examples and their abbreviations are listed below.

[(A) Polymerizable Monomer]
Bis-GMA: 2,2-bis [4-(3-methacryloyloxy-2-hydroxypropoxy) phenyl] propane 2.6E: 2,2-bis (4-(meth) acryloyloxy polyethoxyphenyl) propane in which the average addition mole number of ethoxy groups is 2.6
UDMA: N,N-(2,2,4-trimethyl hexamethylene) bis [2-(aminocarboxy) ethanol]methacrylate
NPG: neopentyl glycol dimethacrylate
TEGDMA: triethyleneglycol dimethacrylate <(A1) Polymerizable Monomer Having an Acidic Group>
MDP: 10-methacryloyloxydecyl dihydrogen phosphate
MHPA: 6-methacryloxyhexyl phosphonoacetate
MET: 4-methacryloxyethyl trimellitic acid
META: 4-methacryloxyethyl trimellitic anhydride
AET: 4-acryloyloxyethyltrimellitic acid
SAME: mono (2-acryloyloxyethyl) succinate

[(B) Photosensitizer]
CQ: camphorquinone
BAPO: phenyl bis (2,4,6-trimethylbenzoyl) phosphine oxide

[(C) Photoacid Generator]
<Salt of an Anion Having an Organic Group in which at Least One H is Substituted with F and One or More Atoms of P, B, Al, S, and Ga, and an Aryl Iodonium Cation>

C1: bis (4-tert-butylphenyl) iodonium nonafluorobutane sulfonate

[Chemical formula 5]

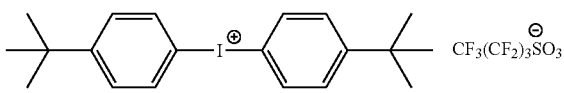

C2: bis (4-tert-butylphenyl) iodonium tris (pentafluoropropyl) trifluorophosphate

[Chemical formula 6]

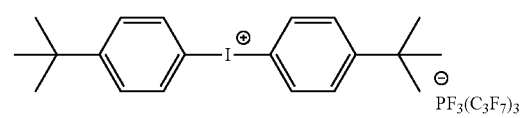

C3: p-cumenyl (p-tolyl) iodonium tris (pentafluoroethyl) trifluorophosphate

[Chemical formula 7]

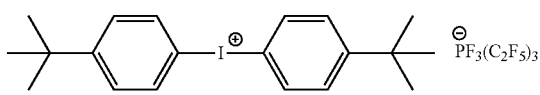

C4: p-cumenyl (p-tolyl) iodonium tetrakis (pentafluorophenyl) borate

[Chemical formula 8]

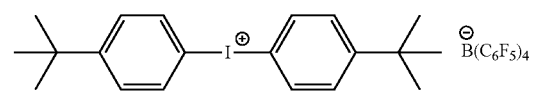

C5: bis [(4-tert-butyl) phenyl] iodonium tetra (nonafluoro-tert-butoxy) aluminate

[Chemical formula 9]

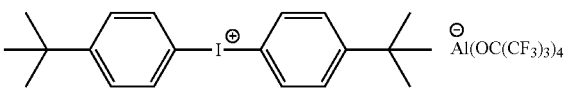

C6: bis [4-(tert-butyl) phenyl] iodonium tetra (pentafluorophenyl) gallate

[Chemical formula 10]

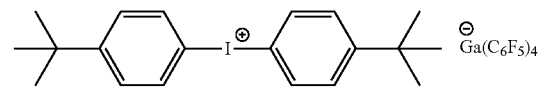

<Salt of an Anion Having an Organic Group and One or More Atoms of P, B, Al, S, and Ga, and an Aryl Iodonium Cation>

C11: bis (4-tert-butylphenyl) iodonium-p-toluenesulfonate

[Chemical formula 11]

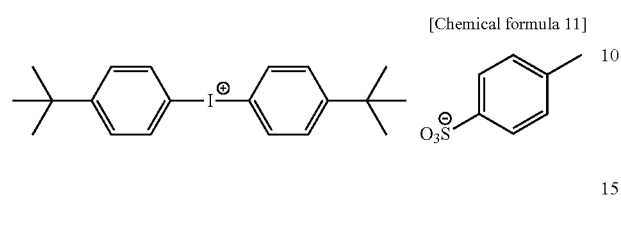

<Photoacid Generator which is not a Salt of an Anion Having an Organic Group and One or More Atoms of P, B, Al, S, and Ga, and an Aryl Iodonium Cation>

C21: diphenyl iodonium hexafluorophosphate

[Chemical formula 12]

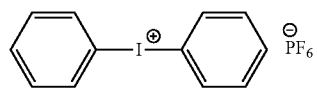

C22: 2,4,6-tris (trichloromethyl)-1,3,5-triazine

[Chemical formula 13]

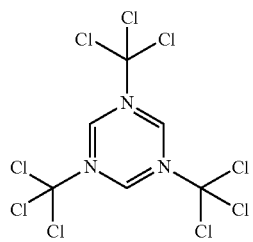

C23: diphenyliodonium-2-carboxylate monohydrate

[Chemical formula 14]

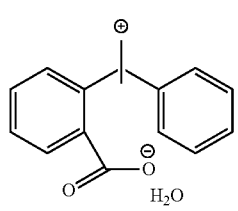

[(D) Photopolymerization Accelerator]

Log P of tertiary aliphatic amine compound and pKa of the amine were calculated using ChemDraw Professional ver 18.1. In the case of a compound having a hydroxy group in the molecule, a smaller value was adopted as pKa. Further, in the case of a compound having two or more pKa by having two or more N atoms derived from amine in the molecule, a higher value was adopted.

[(D1) Tertiary Aliphatic Amine Compound Having Log P of 2 or More and pKa of 10 or Less]

D1-1: tribenzylamine (Log P: 5.44, pKa: 8.574)

[Chemical formula 15]

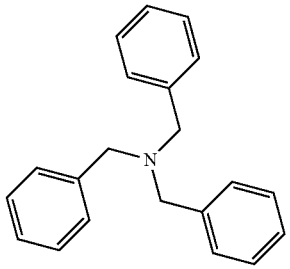

D1-2: dibenzyl glycine ethyl (Log P: 3.58, pKa 5.960)

[Chemical formula 16]

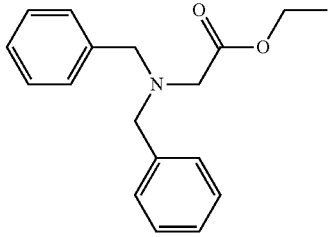

D1-3: dibenzyl methylamine (Log P: 3.71, pKa: 9.094)

[Chemical formula 17]

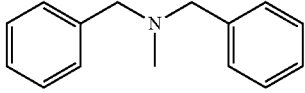

D1-4: 1-[(3,3-diphenylpropyl) (methyl) amino]-2-methyl-2-propanol (Log P: 4.21, pKa: 9.288)

[Chemical formula 18]

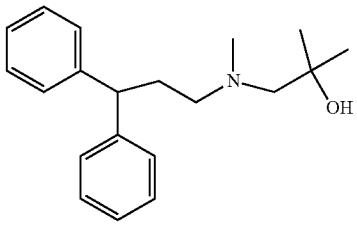

D1-5: 2-benzyl-6-oxo-1-phenyl-5,10-dioxo-2,7-diazadodecane-12-yl methacrylate (Log P: 3.92, pKa: 7.687)

After putting 5.0 g of dibenzyl ethanolamine, 4.1 g of 2-(2-methacryloyloxy ethyloxy) ethylisocyanate and 0.0091 g of p-methoxyphenol with 9 g of toluene into 50 mL eggplant-shaped flask, the mixture was stirred at 50° C. for one week. Then, toluene was distilled off using a rotary evaporator to obtain the target compound D1-5.

[Chemical formula 19]

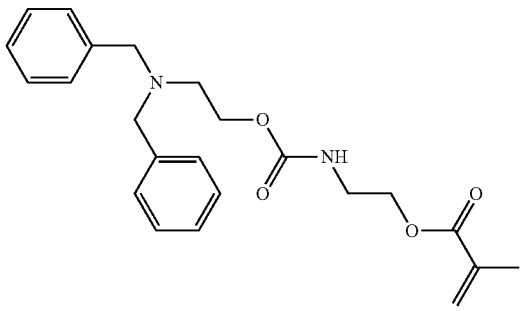

D1-6: 3-(dibenzylamino) propylmethacrylate (Log P: 4.56, pKa: 8.557)

After putting 5.0 g of 3-(dibenzylamino) propan-1-ol, 7.8 g of methyl methacrylate and 0.0064 g of p-methoxyphenol, 0.0830 g of anhydrous potassium phosphate and 15 mL of toluene into a 50 mL eggplant-shaped flask, Dimroth condenser was attached and the mixture was stirred at 70° C. for 4 hours. Then, methanol, which was a by-product, was removed from the reaction solution by a vacuum distillation operation. The progress of the reaction was confirmed by gas chromatography analysis, and methyl methacrylate was added to the reaction solution so that the molar ratio of methyl methacrylate to 3-(dibenzylamino) propan-1-ol was the same as at the start of the reaction, and stirred again at 70° C. for 4 hours. Then, unreacted methyl methacrylate, methanol as a by-product, and toluene as a solvent were removed from the reaction solution by a vacuum distillation operation. The prepared suspension was suction-filtered to obtain the target compound D1-6.

[Chemical formula 20]

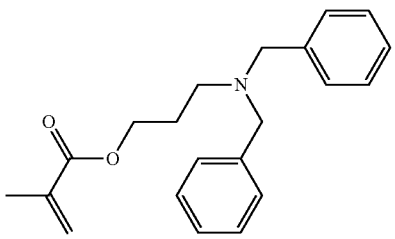

D1-7: tetramethyl methylpiperidyl methacrylate (Log P: 2.01, pKa: 9.453)
D1-8: stearyldiethanolamine (Log P: 6.29, pKa: 8.583)
D1-9: N,N-diisopropyl aminoethyl methacrylate (Log P: 6.29, pKa: 8.583)

[Tertiary Aliphatic Amine Compound Having Log P of Less than 2 or pKa of More than 10]
D2-1: diethylaminoethyl methacrylate (Log P: 1.67, pKa: 8.939)
D2-2: dimethylamino propylacrylamide (Log P: 1.275, pKa: 9.676)
D2-3: methyldiethanolamine (Log P: −0.79, pKa: 8.524)
D2-4: 1,4-diazabicyclo [2.2.2] octane (Log P: 0.34, pKa: 8.976)
D2-5: dicyclomethylamine (Log P: 3.34, pKa: 10.196)
D2-6: dimethyl octadecylamine (Log P: 7.33, pKa: 10.198)
D2-7: triethylamine (Log P: 1.26, pKa: 10.225)

[Polymerization Accelerator Other than Tertiary Aliphatic Amine Compound (Aromatic Tertiary Amine Compounds)]
DMBE: ethyl N,N-dimethylaminobenzoate

[(E) Filler]
The preparing method of each filler used for preparing the dental photocurable composition is shown below.

(Filler E1)
A silane coupling treatment solution prepared by stirring 50.0 g of water, 35.0 g of ethanol, and 3.0 g of 3-methacryloyloxypropyl trimethoxysilane as a silane coupling material at room temperature for 2 hours was added to 100.0 g of fluoroaluminosilicate glass (average particle diameter: 1.1 µm) and stirred for 30 minutes. Thereafter, a heat treatment was performed at 100° C. for 15 hours to obtain filler E1.

(Filler E2)
A silane coupling treatment solution prepared by stirring 50.0 g of water, 35.0 g of ethanol, and 5.0 g of 3-methacryloyloxypropyl trimethoxysilane as a silane coupling material at room temperature for 2 hours was added to 100.0 g of the zirconium silicate filler (average particle diameter: 0.8 µm, zirconia: 85 wt. %, silica: 15 wt. %) and stirred for 30 minutes. Thereafter, a heat treatment was performed at 100° C. for 15 hours to obtain filler E2.

(Filler E3)
After various raw materials of silica dioxide, aluminum oxide, boron oxide, sodium fluoride, and strontium carbonate were mixed, the mixture was melted to obtain glass A (glass composition: $SiO_2$ 22.5% by mass, $Al_2O_3$ 20.0% by mass, $B_2O_3$ 12.3% by mass, SrO 35.7% by mass, $Na_2O$ 2.5% by mass, and F 7.0% by mass). The obtained glass A was pulverized using a vibration mill for 100 hours, and then pulverized using a wet bead mill for 3 hours. Then, 4.5 g of a low condensate of silane compound "MKC SILICATE MS56S" ($SiO_2$ content: 56.0% by mass, degree of polymerization: 2 to 100, manufactured by Mitsubishi Chemical Corporation) was added to 100 g of the obtained pulverized product, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and pulverized at 1800 rpm for 5 minutes. After pulverization, a polysiloxane-treated material having good fluidity was obtained.

(Acidic Polymer Treatment)
Then, 100 g of the polysiloxane-treated product was put into a Henschel mixer, and 16.0 g of an aqueous polyacrylic acid solution (polymer concentration: 13% by mass, weight average molecular weight: 20,000; manufactured by Nacalai Co., Ltd.) was sprayed from above while stirring. After spraying, the powder taken out from the mixer was heated in a hot air dryer at 100° C. for 3 hours to obtain a polysiloxane-polyacrylic acid-treated product.

(Silane Treatment)
A silane coupling treatment solution prepared by stirring 100.0 g of water, 80.0 g of ethanol, 0.003 g of phosphoric acid, and 12.0 g of 8-methacryloyloxypropyl trimethoxysilane as a silane coupling agent at room temperature for 2 hours was added to 100.0 g of the polysiloxane-polyacrylic acid-treated product and stirred for 30 minutes. Thereafter, a heat treatment was performed at 100° C. for 15 hours to obtain filler E3.

(Filler E4)
A silane coupling treatment solution prepared by stirring 100.0 g of water, 80.0 g of ethanol, 0.003 g of phosphoric acid, and 12.0 g of 8-methacryloyloxy octyltrimethoxysilane as a silane coupling agent at room temperature for 2 hours was added to 100.0 g of the above polysiloxane-treated product and stirred for 30 minutes. Thereafter, a heat treatment was performed at 100° C. for 15 hours to obtain filler E4.

(Filler E5)
  Aerosil R8200 (manufactured by Evonik)
(Filler E6)
  Aerosil R711 (manufactured by Evonik)
(Filler E7)
  Aerosil AluC805 (manufactured by Evonik)

[Uv Absorber]
  BT: 2-(2-hydroxy-5-methylphenyl) benzotriazole
[Polymerization Inhibitor]
  MeHQ: p-methoxyphenol
[Fluorescent Agent]
  FA: 2.5-dihydroxyterephthalate diethyl <Preparing Method of Matrix>

All components shown in Tables 1 to 2 other than the filler (E) were put into a wide mouthed plastic container and mixed by using a mix rotor VMRC-5 under the condition of 100 rpm for 48 hours to prepare a matrix. In the Tables 1 to 2, the content (parts by mass) of each component is indicated by the numerical value in parentheses after the abbreviation of each component.

<Preparing Method of Dental Photocurable Composition>

All components shown in Tables 1 to 2 other than the filler (E) were mixed to prepare a matrix. Then, the matrix and the filler (E) were put into a rotation and revolution kneader, stirred, and then defoamed under vacuum to prepare a paste, and then the paste was filled into 2 mL syringe made of PP to prepare a dental photocurable composition. In the Tables 1 to 2, the content (parts by mass) of each component is indicated by the numerical value in parentheses after the abbreviation of each component.

TABLE 1

| One pack type dental photocurable composition | (A) Polymerizable monomer other than (A1) | (A1) Polymerization monomer having an acidic group | (B) photo sensitizer | (C) photoacid generator | (D) Photopolymerization accelerator — (D1) Tertiary aliphatic amine compound having LogP of 2 or more and pKa of 10 or less | Photopolymerization accelerator other than (D1) | Polymerization inhibitor | Others | (E) Filler |
|---|---|---|---|---|---|---|---|---|---|
| Example 1 | Bis-GMA(40), NPG(40), UDMA(18) | MDP(2) | CQ(0.2) | C2(2) | D1-1(1) | — | MeHQ(0.01) | FA(0.01) | E1(200) |
| Example 2 | Bis-GMA(40), NPG(40), UDMA(19) | MET(1) | CQ(0.01) | C25.5) | D1-1(5.5) | — | MeHQ(0.01) | FA(0.01) | E2(200) |
| Example 3 | Bis-GMA(40), NPG(40), UDMA(19) | MET(1) | CQ(0.8) | C1(0.15) | D1-1(0.5) | — | MeHQ(0.005) | FA(0.01) | E3(200) |
| Example 4 | Bis-GMA(40), NPG(40), UDMA(19) | MDP(1) | CQ(1.1) | C2(0.05) | D1-1(4) | — | MeHQ(0.005) | FA(0.01) | E4(200) |
| Example 5 | Bis-GMA(40), NPG(40), UDMA(18) | MHPA(2) | CQ(0.2) | C2(4) | D1-2(0.05) | DMBE(0.1) | MeHQ(0.005) | FA(0.01) | E1(150), E5(15) |
| Example 6 | Bis-GMA(40), NPG(40), UDMA(18) | MDP(2) | CQ(0.04) | C24 | D1-2(4) | — | MeHQ(0.005) | FA(0.01) | E4(150), E5(15) |
| Example 7 | 2,6E(79.9), TEGDMA(20) | MDP(0.1) | CQ(0.8) | C24 | D1-2(0.1) | — | — | FA(0.01) | B4(300), E6(10) |
| Example 8 | Bis-GMA(59), TEGDMA(40) | AET(1) | CQ(0.3) | C11(1.5) | D1-1(0.6) | — | MeHQ(0.005) | FA(0.01) | E1(150), E5(15) |
| Example 9 | Bis-GMA(59), TEGDMA(40) | AET(1) | CQ(0.3) | C21(1.1) | D1-2(0.9) | — | MeHQ(0.005) | FA(0.01) | E3(250), E6(10) |
| Example 10 | Bis-GMA(59), TEGDMA(40) | AET(1) | CQ(0.25) | C22(1.2) | D1-1(1) | — | MeHQ(0.005) | FA(0.01) | E1(200), E6(10) |
| Example 11 | Bis-GMA(59), TEGDMA(40) | AET(1) | CQ(0.25) | C23(1.3) | D1-5(1) | — | MeHQ(0.005) | FA(0.01) | E2(200), E3(15) |
| Example 12 | UDMA(68), TEGDMA(30) | AET(2) | CQ(0.2) | C3(2) | D1-1(2) | — | MeHQ(0.005) | FA(0.01) | E2(200), E3(15) |
| Example 13 | Bis-GMA(59), TEGDMA(40) | AET(1) | CQ(0.2) | C4(0.6) | D1-1(2) | — | MeHQ(0.005) | FA(0.01) | E1(200), E3(15) |
| Example 14 | UDMA(68), TEGDMA(30) | MET(1) | CQ(0.1) | C5(0.7) | D1-1(1.5) | — | — | FA(0.01) | E2(300), E6(10) |
| Example 15 | UDMA(69.5), TEGDMA(30) | SAME(0.5) | CQ(0.15) | C6(0.8) | D1-1(1) | — | MeHQ(0.005) | — | E1(200), E6(10) |
| Example 16 | UDMA(69.5), TEGDMA(30) | MET(0.5) | CQ(0.2) | C4(0.5) | D1-1(2) | — | MeHQ(0.005) | — | E2(300), E6(10) |
| Example 17 | UDMA(69.5), TEGDMA(30) | MET(0.5) | CQ(0.2) | C5(0.5) | D1-1(2) | — | MeHQ(0.005) | — | E2(300), E6(10) |
| Example 18 | Bis-GMA(39.5), NPG(40), UDMA(20) | AET(0.5) | CQ(0.1) | C1(3) | D1-1(2) | — | MeHQ(0.005) | FA(0.01) | B4(180), E3(20) |
| Example 19 | Bis-GMA(60), TEGDMA(39.995) | MDP(0.005) | CQ(0.15) | C1(2) | D1-2(1) | — | MeHQ(0.005) | FA(0.01) | E2(200), E3(10) |
| Example 20 | UDMA(55), TEGDMA(35) | MHPA(10) | CQ(0.2) | C1(2) | D1-3(3) | — | MeHQ(0.005) | — | E2(200), E3(5) |
| Example 21 | Bis-GMA(60), TEGDMA(35) | MHPA(5) | CQ(0.2) | C1(2) | D1-3(3) | — | MeHQ(0.005) | — | B4(200), E6(10) |
| Example 22 | 2,6E(74.5), TEGDMA(25) | MDP(0.5) | CQ(0.15) | C1(2) | D1-4(1) | — | MeHQ(0.005) | — | B4(200), E7(10) |
| Example 23 | UDMA(69.5), TEGDMA(30) | MET(0.5) | CQ(0.2) | C3(1) | D1-5(1) | — | MeHQ(0.005) | — | E1(300), E7(5) |
| Example 24 | UDMA(69.5), TEGDMA(30) | MET(0.5) | CQ(0.15) | C3(1) | D1-7(1) | — | MeHQ(0.005) | — | B4(200), E5(10) |
| Example 25 | Bis-GMA(60), TEGDMA(39.995) | MDP(0.005) | CQ(0.2) | C3(1) | D1-7(1.5) | — | MeHQ(0.005) | FA(0.01) | E2(200), E6(10) |
| Example 26 | Bis-GMA(60), TEGDMA(39.995) | MDP(0.005) | CQ(0.15) | C3(1) | D1-8(1) | — | MeHQ(0.005) | FA(0.01) | E4(170), E3(30), E5(10) |
| Example 27 | Bis-GMA(60), TEGDMA(38) | MDP(2) | CQ(0.2) | C6(0.9) | D1-6(1) | — | MeHQ(0.005) | — | E2(170), E3(30), E5(10) |
| Example 28 | Bis-GMA(60), TEGDMA(39.9) | MDP(0.1) | CQ(0.15) | C3(1) | D1-6(1) | — | MeHQ(0.005) | — | E2(190), E3(20), E5(10) |
| Example 29 | Bis-GMA(59), TEGDMA(40) | AET(1) | CQ(0.2) | C3(1.5) | D1-6(1) | DMBE(0.2) | MeHQ(0.005) | FA(0.01) | E1(200), E3(20), E6(10) |
| Example 30 | Bis-GMA(60), TEGDMA(35) | SAME(5) | CQ(0.15) | C3(1) | D1-6(1.3) | DMBE(0.2) | MeHQ(0.005) | FA(0.01) | E4(200), E3(10), E6(10) |
| Example 31 | Bis-GMA(60), TEGDMA(30) | AET(1) | CQ(0.2) | C21.5) | D1-9(1.5) | DMBE(0.2) | MeHQ(0.005) | FA(0.01) | E2(200), E420), E6(10) |
| Example 32 | Bis-GMA(60), TEGDMA(38) | MDP(2) | CQ(0.2) | C40.5) | D1-1(0.5) | — | MeHQ(0.005) | FA(0.01) | E1(300), E6(10) |
| Example 33 | UDMA(50), TEGDMA(49.5) | SAME(0.5) | CQ(0.2) | C3(1) | D1-2(1) | — | MeHQ(0.005) | — | E4(550) |
| Example 34 | Bis-GMA(59), TEGDMA(40) | AET(1) | CQ(0.2) | C21.5) | D1-2(1) | — | MeHQ(0.005) | FA(0.01), BT(0.5) | B4(200), E3(20) |
| Example 35 | UDMA(69.995), TEGDMA(30) | MHPA(0.005) | CQ(0.1) | C3(1) | D1-7(1.5) | — | MeHQ(0.005) | FA(0.01), BT(0.5) | E3(5), E5(10) |
| Example 36 | UDMA(65), TEGDMA(25) | MHPA(10) | CQ(0.2) | C3(1) | D1-4(2) | — | MeHQ(0.005) | FA(0.01), BT(0.5) | E3(5), E5(10) |
| Example 37 | Bis-GMA(30), UDMA(30), TEGDMA(37) | MDP(2), META(1) | CQ(0.2) | C21.5) | D1-7(1.5) | — | MeHQ(0.005) | — | E3(5), E5(10) |
| Example 38 | Bis-GMA(30), UDMA(30), TEGDMA(37) | MHPA(2), META(1) | CQ(0.2) | C3(1) | D1-4(1) | — | MeHQ(0.005) | — | E3(30), E7(10) |

TABLE 2

| One pack type dental photocurable composition | (A) Polymerization monomer — Polymerizable monomer other than (A1) | (A) Polymerization monomer — (A1) Polymerization monomer having an acidic group | Photopolymerization initiator (B) photo sensitizer | Photopolymerization initiator (C) photoacid generator | Photopolymerization initiator (D) Photopolymerization accelerator (D1) Tertiary aliphatic amine compound having LogP of 2 or more and pKa of 10 or less |
|---|---|---|---|---|---|
| Example 39 | UDMA(67), TEGDMA(30) | MDP(2), SAME(1) | CQ(0.2) | C2(1.5) | D1-1(2) |
| Example 40 | UDMA(68), TEGDMA(30) | META(2) | CQ(0.2) | C3(1) | D1-3(3) |
| Example 41 | Bis-GMA(30), UDMA(30), TGDMA(37) | MHPA(1.5), MET(1.5) | CQ(0.1) | C3(1) | D1-4(1) |
| Example 42 | Bis-GMA(67), TEGDMA(30) | MHPA(3) | CQ(0.2) | C2(1.5) | D1-5(1) |
| Example 43 | Bis-GMA(40), NPG(40), UDMA(18) | MDP(2) | CQ(0.05) | C2(2) | D1-1(1) |
| Example 44 | Bis-GMA(40), NPG(40), UDMA(18) | MDP(2) | CQ(0.5) | C2(2) | D1-1(1) |
| Example 45 | Bis-GMA(40), NPG(40), UDMA(18) | MDP(2) | CQ(0.02) | C2(4) | D1-1(4) |
| Example 46 | Bis-GMA(40), NPG(40), UDMA(19) | MET(1) | CQ(1) | C1(0.15) | D1-1(0.5) |
| Example 47 | Bis-GMA(40), NPG(40), UDMA(18) | MDP(2) | CQ(0.2) | C2(5) | D1-1(1) |
| Example 48 | Bis-GMA(40), NPG(40), UDMA(18) | MDP(2) | CQ(0.5) | C2(0.2) | D1-1(1) |
| Example 49 | Bis-GMA(40), NPG(40), UDMA(19) | MET(1) | CQ(0.8) | C1(0.1) | D1-1(0.5) |
| Example 50 | Bis-GMA(40), NPG(40), UDMA(18) | MDP(2) | CQ(0.2) | C2(2) | D1-1(5) |
| Example 51 | Bis-GMA(40), NPG(40), UDMA(18) | MDP(2) | CQ(0.2) | C2(2) | D1-1(0.5) |
| Comparative Example 1 | Bis-GMA(58), TEGDMA(40) | MDP(2) | — | C2(0.7) | D1-1(1) |
| Comparative Example 2 | UDMA(69), TEGDMA(30) | SAME(1) | CQ(0.5) | — | D1-1(1.5) |
| Comparative Example 3 | UDMA(69), TEGDMA(30) | SAME(1) | CQ(0.3) | C5(2) | — |
| Comparative Example 4 | UDMA(69), TEGDMA(30) | MDP(1) | CQ(0.3) | C5(3) | — |
| Comparative Example 5 | Bis-GMA(60), TEGDMA(40) | — | CQ(0.3) | C2(2) | — |
| Comparative Example 6 | UDMA(70), TEGDMA(30) | — | CQ(0.3) | C1(2) | — |
| Comparative Example 7 | Bis-GMA(60), TEGDMA(40) | — | CQ(0.3) | C4(2) | — |
| Comparative Example 8 | UDMA(70), TEGDMA(30) | — | CQ(0.3) | C1(2) | — |
| Comparative Example 9 | Bis-GMA(60), TEGDMA(40) | — | CQ(0.3) | C2(2) | — |
| Comparative Example 10 | UDMA(70), TEGDMA(30) | — | CQ(0.3) | C1(2) | — |
| Comparative Example 11 | Bis-GMA(60), TEGDMA(40) | — | CQ(0.3) | C2(5) | D1-8(4) |
| Comparative Example 12 | UDMA(70), TEGDMA(30) | — | CQ(0.3) | C1(2) | — |

| One pack type dental photocurable composition | Photopolymerization initiator (D) Photopolymerization accelerator Photopolymerization accelerator other than (D1) | Polymerization inhibitor | Others | (E) Filler |
|---|---|---|---|---|
| Example 39 | — | MeHQ(0.005) | — | E3(5), E5(10) |
| Example 40 | — | — | — | E3(5), E5(10) |
| Example 41 | — | MeHQ(0.005) | — | E3(5), E5(10) |
| Example 42 | — | MeHQ(0.005) | — | E5(0.5) |
| Example 43 | — | MeHQ(0.01) | FA(0.01) | E1(200) |
| Example 44 | — | MeHQ(0.01) | FA(0.01) | E1(200) |
| Example 45 | — | MeHQ(0.005) | FA(0.01) | E4(150), E3(15) |
| Example 46 | — | MeHQ(0.005) | FA(0.01) | E3(200), E5(15) |
| Example 47 | — | MeHQ(0.01) | FA(0.01) | E1(200), E3(15) |
| Example 48 | DMBE(0.2) | MeHQ(0.01) | FA(0.1), BT(0.5) | E1(200), E5(15) |
| Example 49 | DMBE(0.1) | MeHQ(0.005) | FA(0.1), BT(0.5) | E3(200) |
| Example 50 | — | MeHQ(0.01) | FA(0.01) | E1(200), E3(15) |
| Example 51 | — | MeHQ(0.01) | FA(0.01) | E1(200), E5(15) |
| Comparative Example 1 | — | MeHQ(0.005) | FA(0.01) | E4(200), E5(10) |
| Comparative Example 2 | — | MeHQ(0.005) | FA(0.01) | E4(200), E5(10) |
| Comparative Example 3 | — | MeHQ(0.005) | FA(0.01) | E1(200) |

TABLE 2-continued

| | | | | |
|---|---|---|---|---|
| Comparative Example 4 | D2-5(5) | — | FA(0.01) | E4(200) |
| Comparative Example 5 | D2-2(3) | MeHQ(0.005) | FA(0.01) | E2(200), E3(20) |
| Comparative Example 6 | D2-1(2) | MeHQ(0.75) | FA(0.01) | E4(200), E3(10) |
| Comparative Example 7 | D2-3(2) | — | FA(0.01) | E4(200), E3(10) |
| Comparative Example 8 | D2-5(2) | — | FA(0.01) | E4(200), E3(10) |
| Comparative Example 9 | D2-6(2) | — | FA(0.01) | E2(300) |
| Comparative Example 10 | D2-7(2) | — | FA(0.01) | E2(300), E5(20) |
| Comparative Example 11 | — | — | FA(0.01) | E2(300), E5(20) |
| Comparative Example 12 | D2-4(1.5) | — | FA(0.01) | E4(200), E3(10) |

TABLE 3

| | Storage stability of matrix | Flexural strength (MPa) | Flexural strength change rate in Accelerated test 1 % | Flexural strength change rate in Accelerated test 2 % | Thermal color stability | Color stability after irradiation |
|---|---|---|---|---|---|---|
| Example 1 | A | 126 | −0.8 | −0.3 | A | A |
| Example 2 | A | 82 | −2.3 | −1.2 | A | C |
| Example 3 | A | 95.0 | −4.0 | −3.0 | A | B |
| Example 4 | A | 82 | −0.8 | 2.0 | A | C |
| Example 5 | A | 92 | −1.7 | −5.0 | A | C |
| Example 6 | A | 93 | −3.6 | −0.7 | A | A |
| Example 7 | A | 82 | −0.7 | −1.8 | A | B |
| Example 8 | A | 120 | 3.7 | −0.1 | A | B |
| Example 9 | A | 127 | −4.1 | −4.4 | A | C |
| Example 10 | A | 126 | −4.7 | −5.4 | A | C |
| Example 11 | A | 114 | 3.3 | −4.9 | A | C |
| Example 12 | A | 120 | −1.7 | −5.0 | A | A |
| Example 13 | A | 124 | −3.7 | −2.5 | A | A |
| Example 14 | A | 120 | 0.8 | −1.1 | A | A |
| Example 15 | A | 119 | −4.2 | −5.1 | A | A |
| Example 16 | A | 122 | −4.7 | −2.2 | A | A |
| Example 17 | A | 118 | −4.7 | 0.9 | A | A |
| Example 18 | A | 120 | −4.2 | −1.9 | A | A |
| Example 19 | A | 121 | −10.8 | −5.1 | A | A |
| Example 20 | A | 101 | −3.0 | −2.8 | A | A |
| Example 21 | A | 112 | −3.6 | 0.7 | A | A |
| Example 22 | A | 121 | −0.8 | −4.8 | A | A |
| Example 23 | A | 124 | −4.1 | −2.4 | A | A |
| Example 24 | A | 116 | −4.0 | 0.2 | A | A |
| Example 25 | B | 131 | −12.8 | −0.6 | A | A |
| Example 26 | B | 120 | −12.5 | −4.7 | B | A |
| Example 27 | A | 122 | −4.8 | −4.1 | A | A |
| Example 28 | A | 118 | −3.1 | −0.5 | A | A |
| Example 29 | A | 130 | −4.3 | 0.0 | A | C |
| Example 30 | A | 131 | −3.4 | −0.4 | A | A |
| Example 31 | A | 125 | 0.0 | −2.6 | A | A |
| Example 32 | A | 120 | −12.5 | −3.8 | A | C |
| Example 33 | A | 131 | −0.8 | −5.3 | A | A |
| Example 34 | A | 125 | −2.1 | −0.2 | A | A |
| Example 35 | B | 97 | −11.6 | −15.4 | A | A |
| Example 36 | A | 91 | 2.2 | −4.4 | A | A |
| Example 37 | A | 98 | −2.1 | −3.1 | A | A |
| Example 38 | A | 96 | 0.9 | 0.8 | A | A |
| Example 39 | A | 101 | −3.4 | 0.4 | A | A |
| Example 40 | A | 100 | −3.6 | −3.6 | A | A |
| Example 41 | A | 99 | 0.9 | −3.8 | A | A |
| Example 42 | A | 98 | 2.6 | −0.8 | A | A |
| Example 43 | A | 109 | 1.1 | 1.2 | A | A |
| Example 44 | A | 128 | 1.2 | 1.4 | A | A |
| Example 45 | A | 91.0 | −2.9 | −1.1 | A | A |
| Example 46 | A | 97.0 | −2.8 | −1.9 | A | B |
| Example 47 | A | 121 | −0.9 | 0.5 | A | A |
| Example 48 | A | 105 | −1.0 | −1.0 | A | A |
| Example 49 | A | 92.0 | 0.5 | −0.5 | A | B |
| Example 50 | A | 115 | 0.5 | 0.5 | A | A |
| Example 51 | A | 105 | −0.9 | −0.5 | A | A |

TABLE 3-continued

|  | Storage stability of matrix | Flexural strength (MPa) | Flexural strength change rate in Accelerated test 1 % | Flexural strength change rate in Accelerated test 2 % | Thermal color stability | Color stability after irradiation |
|---|---|---|---|---|---|---|
| Comparative Example 1 | A | Uncured | Uncured | Uncured | Uncured | Uncured |
| Comparative Example 2 | A | 27 | 22 | −1.0 | A | A |
| Comparative Example 3 | A | 40 | 5 | 0.7 | A | A |
| Comparative Example 4 | D | 105 | Gelation | −13.3 | A | A |
| Comparative Example 5 | D | 107 | Gelation | −25.4 | A | A |
| Comparative Example 6 | A | 32 | −6 | −3.0 | B | A |
| Comparative Example 7 | D | 124 | Gelation | −16.4 | B | A |
| Comparative Example 8 | D | 120 | Gelation | −26.5 | A | A |
| Comparative Example 9 | D | 127 | Gelation | Gelation | A | A |
| Comparative Example 10 | D | 134 | Gelation | −28.1 | A | A |
| Comparative Example 11 | D | 128 | Gelation | −8.2 | B | B |
| Comparative Example 12 | D | 130 | Gelation | −28.0 | A | A |

(1) Storage Stability of Matrix

The prepared matrix was stored in a thermostatic chamber at 50° C., and the presence or absence of gelation was confirmed. Evaluation criteria were as follows.

A (Excellent storage stability): No gelation after storage at 50° C. for 2 months.

B (Good storage stability): No gelation after storage at 50° C. for 1 month.

C (Applicable storage stability): No gelation after storage at 50° C. for 2 weeks.

D (Poor storage stability): Gelation occurred at 50° C. for less than 2 weeks.

In the case that a matrix is gelled, it is not possible to mix the matrix and filler uniformly to prepare a dental photocurable composition. In addition, the longer the period until the matrix gels, the easier it is to handle during manufacturing because the matrix can be stored for a long period of time. For example, it is preferable because changes in the properties of the dental photocurable composition are reduced depending on the timing from the manufacture of the matrix to the mixing with the filler.

(2) Flexural Strength

The prepared dental photocurable composition was filled into a stainless steel mold, and the cover glasses were placed on both sides to press with a glass kneading plate. Thereafter, light was irradiated for 10 seconds to 5 locations by using the photopolymerization irradiator (PEN Bright manufactured SHOFU INC.) to cure the dental photocurable composition. After curing, the cured product was removed from the mold, and light was irradiated to the backside in the same manner again to use as a test specimen (25×2×2 mm rectangular shape). The test specimen was immersed in water at 37° C. for 24 hours, and thereafter flexural test was performed. The flexural test was conducted at a distance between supporting points of 20 mm and at a crosshead speed of 1 mm/min using an Instron universal testing machine (manufactured by Instron). Evaluation criteria were as follows.

Particularly good: 100 MPa or more
Good: 90 or more and less than 100 MPa
Applicable: 80 or more and less than 90 MPa
Insufficient: less than 80 MPa In the case of containing less than 100 parts by mass of the filler with respect to 100 parts by mass of the (A) polymerizable monomer, evaluation criteria were as follows.

Good: 90 MPa or more
Applicable: 70 MPa or more and less than 90 MPa
Insufficient: less than 70 MPa (3) Flexural Strength Change Rate in Accelerated Test 1 (Accelerated Test 1: Storage of Matrix at 50° C. for 2 Weeks)

A dental photocurable composition was prepared using the matrix stored at 50° C. for 2 weeks. The dental photocurable composition was filled into a stainless steel mold, and the cover glasses were placed on both sides to press with a glass kneading plate. Thereafter, light was irradiated for 10 seconds to 5 locations by using the photopolymerization irradiator (PEN Bright manufactured SHOFU INC.) to cure the dental photocurable composition. After curing, the cured product was removed from the mold, and light was irradiated to the backside in the same manner again to use as a test specimen (25×2×2 mm rectangular shape). The test specimen was immersed in water at 37° C. for 24 hours, and thereafter flexural test was performed. The flexural test was conducted at a distance between supporting points of 20 mm and at a crosshead speed of 1 mm/min using an Instron universal testing machine (manufactured by Instron). When the change of flexural strength of the dental photocurable composition from before storage was −10% or more, it was determined to have high storage stability. When the change from before storage was less than −10% to −25%, it was determined that the storage stability was sufficient. When the change from before storage was less than −25% to −40%, it was determined that the storage stability was slightly poor but applicable. When the change from before storage was less than −40%, it was determined that the storage stability was extremely poor and insufficient.

$$((\text{flexural strength after storage (MPa)} - \text{flexural strength before storage (MPa)})/(\text{flexural strength before storage (MPa)})\times 100[\%] \quad [\text{Formula (6)}]$$

(4) Flexural Strength Change Rate in Accelerated Test 2 (Accelerated Test 2: Storage of Dental Photocurable Composition at 50° C. for 2 Weeks)

The prepared dental photocurable composition was stored in a thermostatic chamber at 50° C. for 2 weeks. After 2 weeks, the stored dental photocurable composition was taken out and filled in the stainless mold, and the cover glasses were placed on both sides to press with a glass kneading plate. Thereafter, light was irradiated for 10 seconds to 5 locations by using the photopolymerization irradiator (PEN Bright manufactured SHOFU INC.) to cure the dental curable composition. After curing, the cured product was removed from the mold, and light was irradiated to the backside in the same manner again to use as a test specimen (25×2×2 mm rectangular shape). The test specimen was immersed in water at 37° C. for 24 hours, and thereafter flexural test was performed. The flexural test was conducted at a distance between supporting points of 20 mm and at a crosshead speed of 1 mm/min using an Instron universal testing machine (manufactured by Instron). When the change of flexural strength of the dental photocurable composition from before storage was −10% or more, it was determined to have high storage stability. When the change from before storage was less than −10% to −25%, it was determined that the storage stability was sufficient. When the change from before storage was less than −25% to −40%, it was determined that the storage stability was slightly poor but applicable. When the change from before storage was less than −40%, it was determined that the storage stability was extremely poor and insufficient.

((flexural strength after storage (MPa)−flexural strength before storage (MPa))/(flexural strength before storage (MPa))×100[%]   [Formula (7)]

(5) Thermal Color Stability

Prepared dental photocurable composition was fully filled into a mold (in a shape of a disc having a diameter of 15 mm and a thickness of 1 mm) made of stainless steel. Thereafter, a cover glass was placed on upper side of the stainless mold to apply pressure with glass plate. Subsequently, light irradiation was performed for 1 minute using a photopolymerization irradiator (Grip Light II, manufactured by SHOFU INC.) via the cover glass to prepare a cured material. The cured material was taken out of the mold, the cover glass was removed and the test specimen was measured for color tone. The cured material was taken out of the mold, the cover glass was removed and the test specimen was measured for color tone. Color measurement was performed by placing the test specimen on the background of a standard white plate (D65/10, X=81.07, Y=86.15, Z=93.38) and using a spectrocolorimeter (manufactured by BYK-Chemie GmbH) under predetermined condition (light source: C, viewing angle: 2°, measurement area: 11 mm). Then, the test specimen was immersed in 10 mL of water in a container in a thermostatic chamber set at 70° C., allowed to stand for 1 week, and was measured again for the color tone, and the difference in discoloration was represented by ΔE calculated from the following formula.

$$\Delta E = ((\Delta L^*)^2 + (\Delta a^*)^2 + (\Delta b^*)^2)^{1/2}$$

$$\Delta L^* = L1^* - L2^*$$

$$\Delta a^* = a1^* - a2^*$$

$$\Delta b^* = b1^* - b2^*$$

In the formula, L1* is the brightness index before immersion and stand, L2* is index after immersion and stand, a1*, and b1* are the color quality index before immersion and stand, and a2* and b2* are the color quality index after immersion and stand. Evaluation criteria were as follows.

A (Good): ΔE was less than 10
B (Poor): ΔE was 10 or more

The thermal color stability was measured for predict the color tone change when the cured product was used for a long period of time, and the smaller ΔE, the smaller the color change when the cured product was used for a long period of time. A dental photocurable composition with little color change can be suitably used as a dental material in which aesthetic property is emphasized.

(6) Color Stability after Irradiation

Each prepared dental photocurable composition was fully filled into a mold (in a shape of a disc having a diameter of 15 mm and a thickness of 1 mm) made of stainless steel. Thereafter, a cover glass was placed on upper side of the stainless mold to apply pressure with glass plate. Subsequently, light irradiation was performed for 1 minute using a photopolymerization irradiator (Grip Light II, manufactured by SHOFU INC.) via the cover glass to prepare a cured product. The cured product was taken out of the mold, the cover glass was removed and the test specimen was measured for color tone. Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm). Then, after exposing the test specimen to light for 24 hours with a xenon lamp light exposure tester (Suntest CPS +), the color tone of the test specimen was measured again, and the difference in discoloration was represented by ΔE calculated from the following formula.

$$\Delta E = ((\Delta L^*)^2 + (\Delta a^*)^2 + (\Delta b^*)^2)^{1/2}$$

$$\Delta L^* = L1^* - L2^*$$

$$\Delta a^* = a1^* - a2^*$$

$$\Delta b^* = b1^* - b2^*$$

In the formula, L1* is the brightness index before light exposure, L2* is the brightness index after light exposure, a1* and b1* are the color quality index before light exposure, and a2* and b2* are the color quality index after light exposure. Evaluation criteria were as follows.

A (Good): ΔE was less than 5
B (Applicable): ΔE was 5 or more and less than 8
C (Poor): ΔE was 8 or more The color stability after irradiation was measured for predict the color tone change when the cured product was used for a long period of time in the light exposed area, and the smaller ΔE, the smaller the color change when the cured product was exposed with light for a long period of time. A dental photocurable composition with little color change can be suitably used as a dental material in which aesthetic property is emphasized.

The results shown in Table 3 will be described.

It was confirmed that the compositions described in Examples had sufficient flexural strength and a good storage stability.

In Examples 2, 4, 5, and 7, because the compounding amount of the photosensitizer, photoacid generator, or photopolymerization accelerator was small, there was a tendency that flexural strength was low. In Examples 2 and 4, because the compounding amount of the photosensitizer, photoacid generator, or photopolymerization accelerator was large, there was a tendency that color stability after irradiation was poor.

Among the examples which do not contain a salt of an anion having an organic group in which at least one H was substituted with F and one or more atoms of P, B, Al, S, and Ga, and an aryl iodonium cation as a photoacid generator, there was a tendency that color stability after irradiation slightly decreased in Example 8 containing the photoacid generator C11 which is a salt of an anion having an organic group and one or more atoms of P, B, Al, S, and Ga, and an aryl iodonium cation, and there was a tendency that color stability after irradiation further decreased in Examples 9 to 11 containing other photoacid generator.

In Examples 19, 25, 26, and 35, because the compounding amount of the (A1) polymerizable monomer having an acidic group was small, there was a tendency that flexural strength change rate of the dental photocurable composition prepared using the matrix stored at 50° C. for 2 weeks was low. In addition, in Example 35, because the compounding amount of the (E) filler was small, there was a tendency that flexural strength change rate of the dental photocurable composition stored at 50° C. for 2 weeks was low.

In Examples 20 and 36, because the compounding amount of the (A1) polymerizable monomer having an acidic group was large, the value of flexural strength before the accelerated test was slightly lower in the group having good flexural strength.

Among Examples 5, 29, 30, and 31 containing an aromatic tertiary amine compound as the (D) photopolymerization accelerator, there was a tendency that color stability after irradiation was poor in Examples 5 and 29 containing no ultraviolet absorber, and there was a tendency that color stability after irradiation was excellent in Examples 30 and 31 containing ultraviolet absorber. In addition, in Example 32 containing BAPO other than camphorquinone which is an α-diketone as the (B) photosensitizer, there was a tendency that color stability after irradiation is poor.

In Comparative Examples 1 to 3 not containing any of the photosensitizer, the photoacid generator and the photopolymerization accelerator, these were not cured, or there was a tendency that their flexural strength was remarkably low.

Among Comparative Examples 4 to 10 and 12 not containing the (D1) tertiary aliphatic amine compound having Log P of 2 or more and pKa of 10 or less as the (D) photopolymerization accelerator, gelation was confirmed in the matrix after storage at 50° C. for 2 weeks in Comparative Examples 4, 5, 7, 8, 9, 10 and 12. Therefore, it was not possible to prepare a dental photocurable composition using a matrix stored at 50° C. for 2 weeks. In Comparative Examples 4, 5, 7, 8 and 10, there was a tendency that the flexural strength of the photocurable dental composition stored at 50° C. for 2 weeks decrease significantly. In Comparative Example 9, gelation was confirmed in the dental photocurable composition stored at 50° C. for 2 weeks. In Comparative Example 6, the matrix did not gel after storing at 50° C. for 2 weeks because of containing a large amount of polymerization inhibitor. However, the flexural strength of the prepared dental photocurable composition was remarkably low.

Although Comparative Example 11 contained the (D1) tertiary aliphatic amine compound having Log P of 2 or more and pKa of 10 or less as the (D) photopolymerization accelerator, because of not containing the (A1) polymerizable monomer having an acidic group, gelation was confirmed in the matrix after storage at 50° C. for 2 weeks.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty.

Accordingly, any such changes and modifications are intended to be included in the scope of the embodiments.

INDUSTRIAL APPLICABILITY

The present disclosure may provide a dental photocurable composition capable of achieving both sufficient mechanical strength and storage stability of matrix before preparing the dental photocurable composition.

What is claimed is:

1. A dental photocurable composition, comprising a matrix containing (A) polymerizable monomer, (B) photosensitizer, (C) photoacid generator and (D) photopolymerization accelerator, and (E) filler, wherein,
the dental photocurable composition comprises (A1) polymerizable monomer having an acidic group as the (A) polymerizable monomer, and
the dental photocurable composition comprises (D1) tertiary aliphatic amine compound having Log P of 2 or more and pKa of 10 or less as the (D) photopolymerization accelerator;
wherein the matrix contains 0.1 to 5 parts by mass of the (A1) polymerizable monomer having an acidic group with respect to 100 parts by mass of the (A) polymerizable monomer contained in the matrix.

2. The dental photocurable composition according to claim 1, wherein
an electron-withdrawing group is bonded to one or more of the α-carbon, ß-carbon and γ-carbon bonded to N atom derived from amine in the (D1) tertiary aliphatic amine compound having Log P of 2 or more and pKa of 10 or less, and
the electron-withdrawing group is selected from the group consisting of an aryl group, an ester bond and a urethane bond.

3. The dental photocurable composition according to claim 1, wherein
the dental photocurable composition comprises an aryl iodonium salt as the (C) photoacid generator.

4. The dental photocurable composition according to claim 1, wherein
the (B) photosensitizer contains (B-1) α-diketone compound.

5. The dental photocurable composition according to claim 1, wherein
the dental photocurable composition comprises an aryl iodonium salt as the (C) photoacid generator, and
the aryl iodonium salt is a salt of an anion having an organic group in which at least one H is substituted with F and one or more atoms of P, B, Al, S and Ga, and an aryl iodonium cation.

6. The dental photocurable composition according to claim 1, wherein
the dental photocurable composition does not substantially comprise an aromatic amine compound as the (D) photopolymerization accelerator.

7. The dental photocurable composition according to claim 1, wherein the dental photocurable composition does not substantially comprise a tertiary aliphatic amine compound having Log P of less than 2 or pKa of more than 10 as the (D) photopolymerization accelerator.

8. The dental photocurable composition according to claim 1, wherein a compounding amount of the (E) filler is 30 parts by mass or less with respect to 100 parts by mass of the (A) polymerizable monomer contained in the matrix.

9. The dental photocurable composition according to claim 1, wherein the dental photocurable composition comprises, with respect to 100 parts by mass of the (A) polymerizable monomer contained in the matrix, 0.1 to 5 parts by mass of the (A1) polymerizable monomer having an acidic group, 0.02 to 1 parts by mass of the (B) photosensitizer, 0.1 to 5 parts by mass of the (C) photoacid generator, 0.2 to 5 parts by mass of the (D1) tertiary aliphatic amine compound having Log P of 2 or more and pKa of 10 or less, and 1 to 500 parts by mass of the (E) filler.

10. The dental photocurable composition according to claim 1, wherein the dental photocurable composition comprises, with respect to 100 parts by mass of the (A) polymerizable monomer contained in the matrix, 0.1 to 5 parts by mass of the (A1) polymerizable monomer having an acidic group, 0.02 to 1 parts by mass of the (B) photosensitizer, 0.1 to 5 parts by mass of the (C) photoacid generator, 0.2 to 5 parts by mass of the (D1) tertiary aliphatic amine compound having Log P of 2 or more and pKa of 10 or less, and 1 to 30 parts by mass of the (E) filler.

11. The dental photocurable composition according to claim 1, wherein the dental photocurable composition is used for a dental splinting material.

12. The dental photocurable composition according to claim 1, wherein the dental photocurable composition is prepared by mixing the matrix with the (E) filler after leaving to stand for 2 weeks or more after preparation of the matrix.

13. The dental photocurable composition according to claim 1, wherein the dental photocurable composition comprises a hydrophobized silica fine particle having an average diameter of primary particle of 1 to 40 nm as the (E) filler.

* * * * *